(12) United States Patent
Ransbury et al.

(10) Patent No.: US 6,584,343 B1
(45) Date of Patent: Jun. 24, 2003

(54) MULTI-ELECTRODE PANEL SYSTEM FOR SENSING ELECTRICAL ACTIVITY OF THE HEART

(75) Inventors: Terrance Ransbury, Pleasanton, CA (US); Arne Sippens Groenewegen, Burlingame, CA (US)

(73) Assignee: Resolution Medical, Inc., Pleasanton, CA (US)

( * ) Notice: Subject to any disclaimer, the term of this patent is extended or adjusted under 35 U.S.C. 154(b) by 0 days.

(21) Appl. No.: 09/611,179

(22) Filed: Jul. 6, 2000

Related U.S. Application Data

(60) Provisional application No. 60/189,611, filed on Mar. 15, 2000, and provisional application No. 60/200,965, filed on May 1, 2000.

(51) Int. Cl.[7] .............................................. A61B 5/0402
(52) U.S. Cl. ....................................................... 600/509
(58) Field of Search ................................ 600/509, 510, 600/515–518, 521

(56) References Cited

U.S. PATENT DOCUMENTS

| | | |
|---|---|---|
| 3,565,060 A | 2/1971 | Sipple |
| 4,539,995 A | 9/1985 | Segawa |
| 4,751,471 A | 6/1988 | Dunseath, Jr. |
| 4,751,928 A | 6/1988 | Hallon et al. |
| 4,852,572 A | 8/1989 | Nakahashi et al. |
| 4,865,039 A | 9/1989 | Dunseath, Jr. |
| 4,974,598 A | 12/1990 | John |
| 5,054,496 A | 10/1991 | Wen et al. |
| 5,146,926 A | 9/1992 | Cohen |
| 5,311,873 A | 5/1994 | Savard et al. |
| 5,483,968 A | 1/1996 | Adam et al. |
| 5,634,469 A | 6/1997 | Bruder et al. |
| 5,724,984 A | 3/1998 | Arnold et al. |
| 5,733,151 A | 3/1998 | Edsall et al. |
| 5,772,604 A | 6/1998 | Langberg et al. |
| 5,794,624 A | 8/1998 | Kwong |
| 5,891,049 A | 4/1999 | Cyrus et al. |
| 5,908,393 A | 6/1999 | Albrecht et al. |
| 6,047,206 A | 4/2000 | Albrecht et al. |

FOREIGN PATENT DOCUMENTS

| | | |
|---|---|---|
| WO | WO 97/49143 | 12/1997 |
| WO | WO 98/08274 | 2/1998 |
| WO | WO 99/05962 | 2/1999 |

OTHER PUBLICATIONS

Bagliani et al., "Left Origin of the Atrial Esophageal Signal as Recorded in the Pacing Site" *PACE*–(1998) 21(1):18–24.
Lesh et al., "Comparison of the Retrograde and Transseptal Methods for Ablation of Left Free Will Accessory Pathways" *Journal of American College of Cardiology*, (1993) 22(2):542–549.

(List continued on next page.)

*Primary Examiner*—Jeffrey R. Jastrzab
(74) *Attorney, Agent, or Firm*—Townsend Townsend & Crew LLP; Mark D. Barrish, Esq.

(57) ABSTRACT

Improved systems, devices, and methods sense heart signals through a torso surface of a patient. These improved systems facilitate mounting of an array of sensors upon the patient's torso by supporting the sensor arrays on one or more panels. Four separate panels can be adapted for engaging the torso surface, with the four panels supporting most and/or all of the sensors necessary for localizing an arrhythmia within a chamber of a heart of a patient. The panels may have integrated components for use with other electrophysiology lab equipment such as cardiac imagers, defibrillation power sources, therapeutic probes, standard 12-lead electrocardiogram (ECG) systems, and the like. An exemplary arrhythmia sensing system is adapted for use in the high-noise environment of an electrophysiology lab includes a series of powered circuits distributed among the electrodes of the array. A separate low-noise environment sensing system may initially record an abnormal irregular or regular heartbeat outside the electrophysiology lab.

26 Claims, 14 Drawing Sheets

OTHER PUBLICATIONS

Linnenbank et al., "Choosing the resolution in AD conversion of biomedical signals" *Building Bridges in Electrocardiology,* van Oosterom et al., Eds., Proceedings of the XXIInd International Congress on Electrocardiology, Nijmegen, The Netherlands (Jun. 25–29, 1995) 3 pages total.

Marchlinski et al., "Magnetic Electroanatomical Mapping for Ablation of Focal Atrial Tachycardias" *PACE* (1998) 21:1621–1635.

Meeting van Rijn et al., "High–quality recording of bioelectric events, Part 2: low noise, low–power multichannel amplifier design" *Medical & Biological Engineering & Computing* (1991) 29:433–440.

Metting van Rijn et al., "Patient isolation in multichannel bioelectric recordings by digital transmission through a single optical fiber" *IEEE Transactions on Biomedical Engineering* (1993) 40(3):302–308.

Metting van Rijn et al., "Amplifiers for bioelectric events: A design with minimal number of parts" *Medical & Biological Engineering & Computing* (1994) 32:305–310.

Meurling et al., "Non–invasive Assessment of Atrial Electrophysiology in AF–Influence of Posture Change" *Computers in Cardiology* (1998) 25:637–640.

Peeters et al., "Clinical application of an integrated 3–phase mapping technique for localization of the site of origin of idiopathic ventricular tachycardia" *Circulation* (1999) 99:1300–1311.

Potse et al., "Continuous localization of cardiac activation sites using a database of multichannel ECG recordings" *IEEE Trans. Biomed. Eng.* (Submission date 2000) 8 pages total.

Potse et al., "Software Design for Analysis of Mutichannel Intracardial and Body Surface Electrocardiograms" *Software for Multichannel ECG Analysis* (Draft date 2000) 7 pages total.

Potse et al., "Influence of Chronic Myocardial Infarction on Exit Site Localization of Ventricular Tachycardia Using Paced Body Surace Mappaing" *Proceedings of IEEE Trans. Biomed. Eng.* (Draft date 2000) 3 pages total.

Rodefeld et al., "Global Electrophysiological Mapping of The Atrium: computerized three–dimensional mapping system" *Pacing and Clinical Electrophysiology journal* (1997) 20(9):2227–2236.

Sedaaghi, "ECG Wave Detection Using Morphological Filters" *Applied Sig. Process* (1998) 5:182–194.

Seitman, David T., "Body Surface Potential Map Presentation" *Proc of the N. Engl Bioeng Conf, 4th Yale Univ, New Haven, Conn,* (May 7–8, 1976). pp. 275–278.

SippensGroenewegen et al., "A radiotransparent carbon electrode array for body surface mapping during cardiac catheterization" *Proceedings of the Ninth Annual Conference of the IEEE Engineering in Medicine and Biology Society* (Nov. 13–16, 1987) Boston, MA,, 4 pages total.

SippensGroenewegen et al., "Body Surface Mapping of Ectopic Left and Right Ventricular Activation" *Circulation* 1990) 82(3):879–896.

SippensGroenewegen et al., "Body Surface Mapping of Ectopic Left Ventricular Activation" *Circulation Research* (1992) 71(6):1361–1378.

SippensGroenewegen et al., "Design and Clinical Application of a Body Surface Mapping Reference Data Base for Detailed Localization of Ventricular Tachycardia Foci in Patients Without Structural Cardiac Disease" from Shenasa M, Borggrefe M, and Breithardt G, (eds). *Cardiac Mapping,* Mount Kisco, NY, Futura Publishing Co., Inc., (1993) pp. 347–366.

SippensGroenewegen et al., "Localization of the Site of Origin of Postinfarction Ventricular Tachycardia by Endocardial Pace Mapping" *Circulation* (1993) 88(5):2290–2306.

SippensGroenewegen et al., "Value of body surface mapping in localizing the site of origin of ventricular tachycardia in patients with previous myocardial infarction" *J. Am. Coll. Cardiol.* (1994) 24(7):1709–1724.

SippensGroenewegen et al. "Current Role of On–Line Body Surface Mapping in Postinfarction Ventricular Tachycardia Localization Using Catheter Pace Mapping"; Yasui et al. (Eds.) "Advances in Body Surface Mapping and High Resolution ECG" *Proceedings of Satellite Symposium on Body Surface Mapping and High Resolution Electrocardiography, Yokohama,* (1994) 141–155.

SippensGroenewegen et al., "Body surface mapping during pacing at multiple sites in the human atrium" *Circulation* (1998) 97:369–380.

SippensGroenewegen et al., "Body Surface Mapping of Atrial Arrhythmias" *Journal of Electrocardiology* (Supplement) (1998) 31:85–91.

SippensGroenewegen et al., "Atlas of Paced Body Surface QRS Integral Maps for Localization of the Site of Origin of Postinfarction Ventricular Tachycardia" *Journal of Electrocardiology* vol. 27 Supplement, pp. 105–112.

SippensGroenewegen A., "Database of Body Surface ECG P Wave Integral Maps for Localization of Leftsided Atrial Arrhythmias" (Draft dated 2000) pp. 1–27.

SippensGroenewegen et al., "Body Surface Mapping of Counterclockwise and Clockwise Typical Atrial Flutter: A Comparative Analysis With Endocardial Activation Sequence Mapping," To be published in *Journal of American College of Cardiology,* (Jun. 2000) pp. 1–35.

Tang et al., "Use of P Wave Configuration during Atrial Tachycardia to Predict Site of Origin" *Journal of American College of Cardiology* (1995) 26(5):1315–1324.

Waktare et al., "Optimal Lead Configuration in the Detection and Subtraction of QRS and T Wave Templates in Atrial Fibrillation" *Computers in Cardiology* (1998) 25:629–632.

Yoshida et al., "A Case of Successful Ablation of Ectopic Atrial Tachycardia whose Origin was Detected by Isopotential Mapping" *Respiration and Circulation* (1998) 46(7):717–721.

Hewlett Packard Product Brochure entitled "EASI™ 12–Lead ECG Monitoring" (1999) 2 pages total.

Lifeshirt.com "Vital signs online" (Mar. 30, 2000) http://www.lifeshirt.com/, 1 page total.

Meridian Medical Technologies, Inc. Internet Wire, "Meridian Announces U.S. Clinical Studies with Innovative Prime ECG™ Mapping System" (Mar. 30, 2000) http://www.internetwire.com/technews/me/me990588.dsl, 2 pages total.

Meridian Medical Technologies, Inc. Internet, "Cardiopulmonary Systems" (Mar. 30, 2000) http://www.meridainmeds.com/cardio.html, 2 pages total.

Meridian Medical Technologies, Inc. Internet, "Prime ECG™ The new standard of care in heart attack detection" (Mar. 30, 2000) http://www.meridianmeds.com/prime.htm, 2 pages total.

FIG. 6A Site A ⊕ 4.1 mVrms ⊖ 2.5 mVrms

FIG. 6B Site B ⊕ 3.7 mVrms ⊖ 2.0 mVrms

FIG. 6C Site C ⊕ 3.9 mVrms ⊖ 1.5 mVrms

FIG. 6D Site D ⊕ 3.2 mVrms ⊖ 1.7 mVrms

FIG. 6E Site E ⊕ 6.7 mVrms ⊖ 3.3 mVrms

FIG. 6F Site F ⊕ 5.7 mVrms ⊖ 2.9 mVrms

MULTI-ELECTRODE PANEL SYSTEM FOR SENSING ELECTRICAL ACTIVITY OF THE HEART

CROSS-REFERENCE TO RELATED APPLICATION

The subject matter of this patent application is related to that of co-pending U.S. Provisional Patent Application Nos. 60/189,611 filed Mar. 15, 2000, and 60/200,965 filed May 1, 2000, the full disclosures of which are incorporated herein by reference.

BACKGROUND OF THE INVENTION

I. Field of the Invention

The present invention generally relates to devices, systems, and methods for diagnosing and/or treating the heart. In particular, the invention provides methods and systems for sensing heart signals, and especially for localizing and/or treating arrhythmias.

Significant progress has recently been made toward effective treatments of many cardiac arrhythmias. Contraction of a healthy human heart generally propagates through the heart tissue from the sinus node in the right atrium, and eventually the associated ventricles. This normal propagation of contraction forces blood to flow from the atria to the ventricles in a synchronized pumping action. Arrhythmias of the heart often originate at and/or propagate from alternative heart tissues, resulting in rapid irregular or regular contractions of some or all of the heart. Radiofrequency (RF) intracardiac catheter ablation of the alternative ectopic origin, an abnormal conduction pathway, or an abnormal pathway exit site is now used to effectively treat a variety of arrhythmias.

Although quite effective, current catheter ablation for treatment of cardiac arrhythmias has significant disadvantages. A particular challenge in an effective catheter ablation treatment is the time required for proper identification of the treatment site. Careful mapping of the arrhythmia via multiple catheters is generally required to accurately define the treatment site and limit the size of the ablation. Unfortunately, reliably and repeatedly inducing an arrhythmia can be quite difficult, and can result in a lengthy and unpredictable procedure. As an alternative, candidate ablation sites may be tested during normal sinus rhythm by pace mapping. This testing may be quite time-consuming, as it often involves pacing at several sites with an artificial arrhythmia being initiated using a small electrical pulse from a catheter at each site. The candidate sites are often tested sequentially by positioning the intracardiac catheter against a candidate site within (for example) the right ventricle, identifying the engaged tissue location within the ventricle, sensing and/or pacing the heart cycles at the candidate site, repositioning the intracardiac catheter to a new candidate site, and repeating this process until an ectopic origin or an abnormal pathway exit site has been identified.

As fluoroscopy is often used to identify the location of the engaged tissue, this sequential iterative process can result in significant exposure of the patient and treating personnel to potentially harmful radiation. While alternative (and more complex) intracardiac catheter probe structures have been proposed to allow more rapid identification of the ectopic origin(s) or abnormal pathway exit sites of ventricular tachycardias (VTs) and other arrhythmias, the size and cost of these complex structures may limit their acceptability.

To overcome the disadvantages associated with the known, time consuming and/or invasive intracardiac arrhythmia sensing and localization techniques, researchers have been working on alternative arrhythmia localization techniques which rely on body surfacing mapping, often during pacing. Electrocardiograms (ECGs) may be recorded during abnormal atrial or ventricular activity and compared with ECGs taken during pacing at different sites within the heart to help identify the ectopic site, with the ECGs optionally taken using a standard 12-lead ECG system. More detailed information regarding ectopic sites can be obtained by recording heart cycle signals at the body surface using a more comprehensive sensor array (sometimes called body surface ECG mapping or body surface potential mapping). These heart signals, which generally comprise small amplitude variations in electrical potential along the anterior and/or posterior torso, can be manipulated and/or mapped so as to provide an indication of the origin of the arrhythmia within the heart. Much of this work has concentrated on VT. More recent work has begun to investigate the possibility of localizing certain atrial arrhythmias, such as right atrial tachycardia. U.S. Provisional Patent Application No. 60/189,611, filed Mar. 15, 2000, the disclosure of which is hereby incorporated herein by reference, describes exemplary methods and analysis systems for localization and treatment of atrial fibrillation.

While the new body surface mapping techniques appear quite promising, the sensing systems that have been used to-date to measure the heart cycle signals along the body surface have remained less than ideal. The process of preparing patients by affixing known electrode arrays can be time consuming and difficult, even for the highly skilled researchers now developing these techniques. Additionally, many localization procedures will be performed in an electromagnetically "noisy" environment. For example, the imaging equipment (often biplane fluoroscopy), RF power sources, pacing catheters, and therapeutic probes in use in an electrophysiology lab can induce significant noise in the small amplitude voltage measurements on which many of the new arrhythmia localization techniques are based. These imaging, pacing, and treatment systems may also interfere with the ideal array sensing locations. Undesirable interactions between imaging, treatment and body surface mapping electrode arrays may lead to inconvenience and delays at best, and degraded performance and/or increased dangers to the patient at worst. In other words, while the known body surface mapping systems have been adequate for effective research, improved body surface mapping systems and methods would be desirable to allow these new techniques to be effectively, safely, and reliably applied by practicing doctors for treatment of patients.

In light of the above, it would be desirable to provide improved devices, systems, and methods for sensing heart cycle signals for localization of arrhythmias. It would be particularly beneficial if these improvements enhanced the efficiency of mounting an array upon a patient's torso, as well as increasing the adaptability of the arrays to a variety of patient external anatomies. It would further be beneficial if these improved arrays and body surface mapping methods provided improved safety, reliability, and sensing/localization accuracy, despite the normal variations in physician experience and skill, and without excessive degradation in overall system performance when used in a high electromagnetic noise environment such as an electrophysiology lab. It would further be beneficial to maximize overall system performance without excessive expenditure on individual sensing system components and/or sterilization/reuse procedures. Some or all of these goals are provided by the invention described hereinbelow.

II. Related Art

The following patents and publications may be relevant to the subject matter of the present invention, and their full disclosures are incorporated herein by reference:

U.S. Pat. No. 5,483,968 describes a Method and Apparatus for Analyzing the Electrical Activity of the Heart, and Electrical Clamping Connection Device is described in U.S. Pat. No. 5,733,151. A similar electrode connector is described in PCT Publication No. WO 97/49143. U.S. Pat. No. 6,047,206 which describes Generation of Localized Cardiac Measures, Related Systems, and/or Methods. Similar topics may also be discussed in one or more of U.S. Pat. Nos. 4,751,928; 4,974,598; 5,054,496; 5,634,469; 5,311,873; and 5,724,984.

Arne SippensGroenewegen, et al. described "Body Surface Mapping During Pacing at Multiple sites in the Human Atrium: P Wave Morphology of Ectopic Right Atrial Activation," in Circulation, 98:369–380 (1998). Heidi A. P. Peeters, et al. described related work in an article entitled, "Clinical Application of an Integrated 3-Phase Mapping Technique for Localization of the Site of Origin of Idiopathic Ventricular Tachycardia," in Circulation, 99:1300–1311 (1999). Arne SippensGroenewegen, et al. described "Value of Body Surface Mapping in Localizing the Site of Origin of Ventricular Tachycardia in Patients with Previous Myocardial Infarction," in J. Am. Coll. Cardiol. 24:1708–1724 (1994). "Continuous Localization of Cardiac Activation Sites Using a Database of Multichannel ECG Recordings," was described by Mark Potse, et al. in IEEE Trans. Biomed. Eng., 47:682–689 (2000).

Arne SippensGroenewegen, et al. described "A Radiotransparent Carbon Electrode Array for Body Surface Mapping During Cardiac Catheterization", in the Proceedings of the 9th Annual Conference of IEEE Engineering in Medicine & Biology Society, New York: IEEE Publishing Services, pp. 178–181 (1987). Alexander C. Metting van Rijn, et al. "Patient Isolation in Multichannel Bioelectric Recordings by Digital Transmission Through a Single Optical Fiber," IEEE Trans. Biomed. Eng., 40:302–308 (1993); Alexander C. Metting van Rijn, et al. in "Amplifiers for Bioelectric Events: A Design with a Minimal Number of Parts," Med. & Biol. Eng. & Comput. 32:305–310 (1994); Alexander C. Metting van Rijn, et al. "High-Quality Recording of Bioelectric Events: Part II, Low-Noise, Low-Power Multichannel Amplifier Design," Med & Biol. Eng. & Comput. 29:433–440 (1991); and Andre Linnenbank, et al. "Choosing the Resolution in AD Conversion of Biomedical Signals," Building Bridges in Electrocardiology: Proceedings of the CXXIInd Int'l. Congress on Electrocardiology, eds. A. van Oosterom, T. F. Oostendorp, G. J. H. Uijen, Nijmegen, The Netherlands: University Press Nijmegen, pp. 198–199 (1995), may also be relevant.

SUMMARY OF THE INVENTION

The present invention provides improved systems, devices, and methods for sensing and/or diagnosing arrhythmias of a heart. The improved systems and methods often sense heart signals through a torso surface of a patient. These improved systems generally facilitate mounting of an array of sensors upon the patient's torso by supporting the sensor arrays on one or more panels. In the exemplary embodiment, four separate panels are adapted for engaging the torso surface, with the four panels supporting most or all of the sensors necessary for localizing an arrhythmia within a chamber of a heart of a patient. The panels may have integrated components for use with other electrophysiology lab equipment such as cardiac imagers, defibrillation power sources, therapeutic probes, standard 12-lead electrocardiogram (ECG) systems, and the like. In the exemplary embodiment, an arrhythmia sensing system is adapted for use in the high-noise environment of an electrophysiology lab by including a series of powered circuits distributed among the electrodes of the array. The powered circuits are supported by the panel structure for local amplification, defibrillation protection (often using an electrical energy limiter such as a diode), and the like. Still further functions may be performed locally (in some embodiments) such as conversion of electrical analog signals to digital data and/or optical signals, and the like, or at least some of these functions may instead be performed by a separate transmission signal processing structure between the panels and an arrhythmia analyzer, or even by the analyzer itself. A separate low-noise (and often low-cost) arrhythmia sensing system may be useful for initially recording an abnormal irregular or regular heartbeat outside the electrophysiology lab. These improvements generally enhance the ease of arrhythmia localization, the localization accuracy, and the cost of diagnosis, allowing these highly advantageous body surface mapping techniques to move from academic and research studies to practical tools for treatment of patients.

In a first aspect, the invention provides a sensing system for diagnosing and/or treating a heart of a patient. The patient has a torso surface. The sensing system comprises an array of sensors for sensing heart cycle signals. Four sensor support panels have panel surfaces adapted for engaging the torso surface. The four panels support a majority of the sensors of the array in communication with the torso surface when the panels engage the torso surface.

Preferably, the array will define at least forty (40) sensing locations, with each panel supporting at least 5 sensors, and more preferably at least 7 sensors. The panels can be adapted for alignment with the torso surface, with the sensors of each panel being distributed both along a superior-inferior length and along a lateral width of the panel. The four panels can have leads extending from the sensors for transmitting sensor signals to the analyzer, with the leads preferably extending from each of the panels toward a common lateral side of the patient so as to enhance access to the patient. The leads may optionally comprise a flexible lead material which is selectively deposited or etched along a flexible panel substrate. Ideally, the panels are single-use, disposable structures to avoid the cost and dangers of reuse.

While it is possible to select an appropriate array from a large number of single-panel structures so as to accommodate a particular patient's external anatomy, or to include elastic or other variable size support structures so as to adapt to a wide range of external anatomies, the present application will preferably make use of a limited number (typically two to eight, and ideally four) independent panels. These sets of panels may be selected from a limited number of set sizes, typically from 2 to 10 different sizes, to accommodate different size patients, and ideally from 3 different sizes to accommodate small, medium, and large patients, with the individual panel sizes varying between the different size panel sets. Each panel can comprise a flexible, inelastic substrate, and/or each panel may be mounted independently on the torso surface, typically using a sticky or adhesive torso/panel interface material. This interface may also provide selective electrical coupling of the electrodes of the array to target sensing locations of the torso surface. By independently positioning the panels, a relatively small number of panel sets may be sufficient to accommodate a wide range of patients.

In the exemplary embodiment, severable cross-members of at least some of the panels allow the panel configuration to be modified to accommodate differing external anatomies, (for example, to accommodate breasts and the like). The four panels will ideally each be associated with a quadrant of the torso, for example, providing a right front torso quadrant panel, a left front quadrant panel, a right rear quadrant panel, and a left rear quadrant panel. Still further, alternative structures may be provided to enhance the comfort of many embodiments of the present sensing system, particularly for embodiments intended for extended use. Optionally, such sensing systems may be adapted to provide ambulatory recording for use over a plurality of hours, often for 24 hours or more, and in some cases for 48 hours or more. Such ambulatory recording systems will often comprise a portable power supply (such as a battery) and a portable recording device (such as a non-volatile memory, a magnetic and/or optical recording media and associated drive, or the like).

It will often be advantageous to provide means for accessing the heart cycle signals as measured from the six or twelve standard ECG sensing locations. Such access allows the sensing system to remain in place when using a variety of other electrocardiography systems. The means for accessing may comprise one or more standard or proprietary lead connectors for transmitting sensor signals also used by the arrhythmia analyzer. Alternatively, connectors at the appropriately positioned sensors of the array may be provided, or simple openings in the panel or panels at some or all of the twelve standard lead positions may be included.

In another aspect, the invention provides an apparatus for use with a cardiac stimulation power source and an arrhythmia analyzer for localizing an arrhythmia within a chamber of a heart of a patient. The patient has a torso surface, and the apparatus comprises at least one panel adapted for engaging the torso surface. A cardiac stimulation electrode is mounted to the at least one panel for transmitting energy from the stimulation power source to stimulate the heart. An array of sensors are mounted to the at least one panel. The sensor array transmits sensor signals to the analyzer for localizing the arrhythmia.

In many embodiments, a pair of stimulation or defibrillation electrodes will be mounted to the at least one panel so as to position the heart of the patient between the stimulation electrodes. Often times, one or more sensors of the array will be disposed within a perimeter of the stimulation electrode. Such sensors may be electrically isolated from the stimulation electrode. An imaging window may extend through the panel for imaging of the heart, with at least a portion of the stimulation electrode being disposed within the imaging window. So as to avoid degrading image quality, the portion of the electrode within the imaging window may be adapted to allow imaging therethrough.

In another aspect, the invention provides an apparatus for use with an arrhythmia analyzer and one or more remote imagers when monitoring a patient. The patient has a heart within a torso surface. The apparatus comprises at least one panel having a surface suitable for engaging at least a portion of the torso surface. An array of cardiac signal sensors are mounted to the at least one panel. The sensor array generates signals in response to heart cycle signals for transmission to the arrhythmia analyzer. An imaging window extends through the at least one panel for imaging the heart.

In the exemplary embodiment, a plurality of imaging windows extend through the at least one panel for three-dimensional imaging of the heart, typically using bi-plane fluoroscopy. One or more sensors of the array may be disposed within the imaging window, with such sensors typically being more transparent to the imager than at least some of the sensors disposed beyond the imaging window. For example, sensors within the imaging window may comprise radiotransparent carbon electrodes, while one or more of the sensors disposed beyond the window may comprise a silver/silver chloride electrode. Where powered circuits are distributed among the sensors of the array to avoid noise, the powered circuits will often be disposed outside the imaging window. Similarly, electrical leads within the imaging window may have an enhanced radiotransparency as compared to electrical leads disposed outside the window. For example, thicknesses of leads within the imaging window may be reduced, lead materials may be changed, or the like. Once again, one or more cardiac stimulation electrodes may be mounted to the at least one panel.

In yet another aspect, the invention provides an arrhythmia localization system for diagnosing an arrhythmia of a heart within a torso surface of a patient. The arrhythmia localization system comprises a noisy-environment sensor system, including a substrate for mounting upon the torso surface, an array of sensors mounted to the substrate, and a plurality of powered circuits distributed among the sensor for transmitting sensor signals. An arrhythmia analyzer is coupleable to the powered circuits for identifying a candidate arrhythmia site within a chamber of the heart of the patient.

Optionally, a separate low-noise environment sensor system may also be provided, with the low-noise system including a substrate for mounting upon the torso surface and an array of sensors mounted to the substrate for recording signals during an abnormal irregular or regular heart beat. The arrhythmia analyzer may identify the candidate arrhythmia site in response to the heart cycle signals sensed by the noisy environment sensor system, and in response to the recorded abnormal heart signals.

In a method aspect, the invention provides an arrhythmia localization method comprising engaging at least one panel against a torso of a patient body. Heart cycle signals are sensed with an array of signals supported by at least one panel. An arrhythmia is localized within a chamber of the heart using the sensed heart cycle signals. Typically, the sensed heart cycle signals are processed with a plurality of powered circuits supported by the at least one panel, the powered circuits distributed among the sensors to inhibit noise.

BRIEF DESCRIPTION OF THE DRAWINGS

FIGS. 11A–D illustrate electrical circuits distributed among the electrodes of an array for amplification of signals, conversion of analog to digital signals, and/or the like.

DESCRIPTION OF THE SPECIFIC EMBODIMENTS

While the following description is largely directed to localization and/or treatment of ventricular tachycardia (VT) and/or atrial fibrillation (AFib), the methods, devices, and systems of the present invention may be used for a wide variety of arrhythmias, including both focal and re-entrant arrhythmias (such as those resulting from infarct scars). When used for treatment of re-entrant arrhythmia, treatment may be directed at or near an exit site of a pathway. The invention may, in some cases, be used with pulmonary vein isolation therapies now being developed (in which linear, circumferential, and/or perimeter lesions may isolate one or more pulmonary veins to inhibit propagation from triggers or exit sites in or near the veins) by allowing selection of target veins and/or indicating whether vein isolation should be utilized. The invention is also useful for localizing focal arrhythmias and pathways beyond the pulmonary veins, and may find use for treatment of paroxysmal AFib, chronic AFib, atrial tachycardia, arrhythmias of the ventricles, localizing an insertion point of a concealed accessory pathway, and the like. Some embodiments of the present invention may also find applications in the general cardiology field, including for non-arrhythmia applications such as ischemia detection and localization, risk-stratification, and the like.

Figure 1:
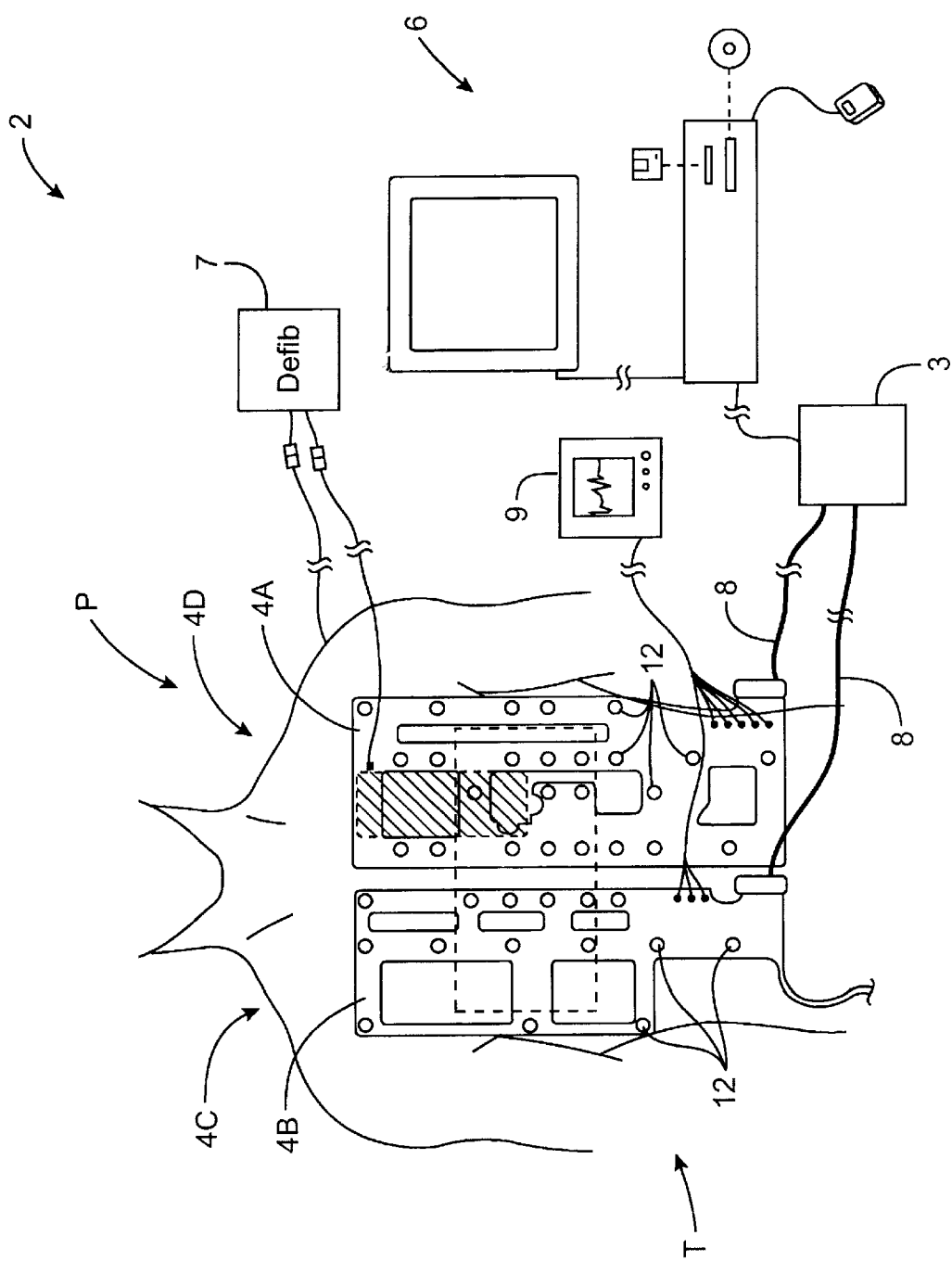
FIG. 1 illustrates a cardiac arrhythmia localization system and method for its use.

Referring now to FIG. 1, an arrhythmia sensing/diagnostic system 2 includes a plurality of panels 4A, 4B, 4C, and 4D (collectively panels 4) which are independently mounted to a torso T of a patient P for diagnosis of an arrhythmia. Each of panels 4 supports a plurality of sensors 12 distributed across the panel. Together, sensors 12 of panels 4 can define an array of sensor locations across the front, sides, and back of torso T of patient P.

Sensors 12 are coupled to an arrhythmia analyzer 6, the arrhythmia analyzer typically comprising a computer (such as a standard PC, Sun® workstation, Silicon Graphics® workstation, or any general purpose or specialized processor of similar or greater computing power) and tangible media having machine readable code with instructions and data for localizing an arrhythmia within a chamber of a heart in response to heart cycle signals sensed by sensors 12. The machine readable code will often comprise hardware, software, and/or firmware, and may optionally make use of proprietary and/or freely available enhancements such as MatLab™ available from the Mathworks, Inc., LabView® available from National Instruments, Inc., or the like. The processor of analyzer 6 will often include some or all the standard components of a general purpose computer, such as one or more input/output ports, a network connection such as an intranet, Ethernet, and/or Internet connection, a reader for tangible media, such as floppy discs, compact optical discs (CDs), or the like, a monitor, a keyboard and/or other input device (such as a mouse, trackball, etc.), and the like. Analyzer 6 will be coupled to panels 4 via cables 8.

Still further exemplary system components are illustrated in FIG. 1, including a data transmitter and/or recorder 3. Transmitter 3 generally comprises an amplifier, an analog to digital converter, an electrical-to-optical signal converter, a power supply (AC/DC), and the like. In the exemplary embodiment, data from sensors 12 is transmitted into this device via electrical cables 8, and is converted to optical signals for transmission to processor 6 along a fiber optic cable. In many embodiments, the signal will be filtered before transmission to the processor.

When panels 4 are used to gather heart signal information in a low-noise environment, data transmitter 3 may alternatively comprise a recording system including a power supply (which may be alternating current and/or direct current such as a battery or the like), a buffer box (to augment signal strength), and a memory (which may comprise a nonvolatile or other digital or analog signal memory, a magnetic and/or optical recording media with associated drive, or the like). Such low-noise systems are particularly useful when gathering data from patients over a long term, typically over two hours or more, and often over one day or even two days or more while the patient remains ambulatory.

As will be described in more detail hereinbelow, panels 4 may be coupled to a defibrillation power source 7, thereby allowing the heart to be defibrillated while panels 4 remain mounted on the patient's torso. This is particularly advantageous when diagnosing and/or treating arrhythmias with techniques which involve artificially initiating an arrhythmia, as it allows the patient to be repeatedly defibrillated as desired. As will also be described hereinbelow, system 2 will often include couplers for transmitting data to a standard ECG analyzer 9. Couplers may be provided on panels 4, using takeoff connectors from cables 8, output ports from the data transmitter or processor, or the like. In some embodiments, panels 4 may simply include openings for independently mounting the standard ECG sensors at the appropriate locations, or the panels may have integrated standard ECG electrodes with dedicated connectors adjacent each standard electrode location.

Figure 1A:
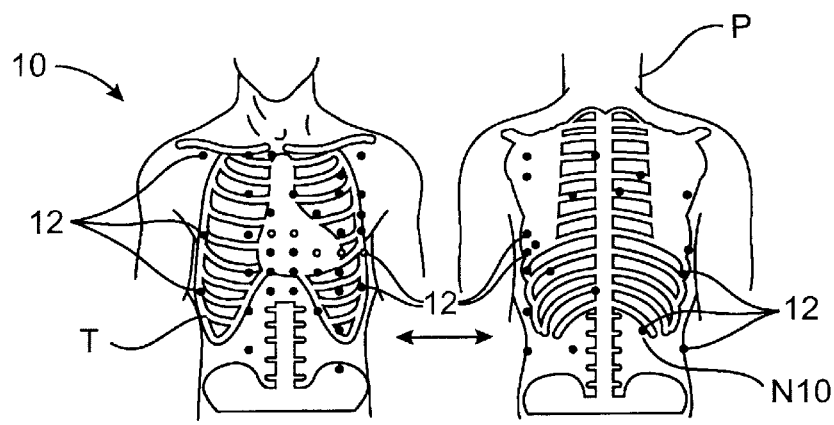
FIG. 1A schematically illustrates a sensor system having an array of sensing locations distributed across a patient's torso.

Referring now to FIG. 1A, the techniques of the present invention will generally make use of an array 10 of sensors 12 distributed across anterior and posterior skin surfaces of torso T on patient P. Array 10 provides multi-lead electrocardiogram (ECG) data at a plurality of sensing locations distributed across torso T, typically at over 20 sensing locations, more preferably at over 40 sensing locations, and ideally at 62 or more sensing locations. Optionally, additional approximated sensor signals may be generated by interpolating between sensors of the array. This may be performed, for example, to generate data at 192 sensing locations when only 62 sensors are present in the array.

Sensors 12 generally comprise unipolar or bipolar electrodes coupled to the patient's skin, or to an alternative accessible tissue surface (for example via a transesophageal approach) suitable for measuring electrical surface potential.

Figure 1C:
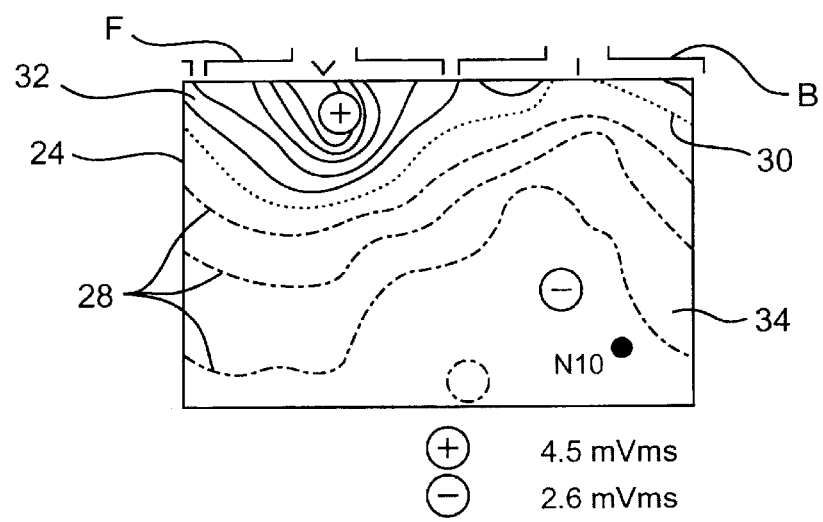
FIG. 1C illustrates a plot of a data matrix generated by mapping the integral values with positions corresponding to the locations of the sensors across the patient's torso.
Figure 1B:
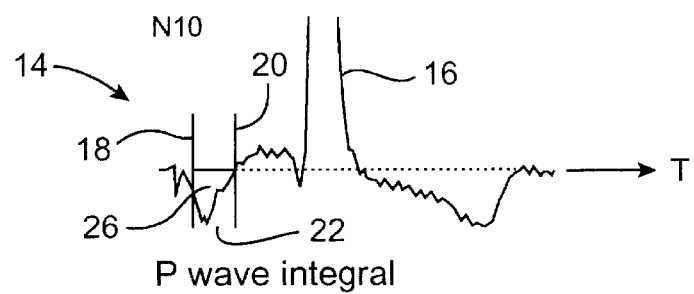
FIG. 1B graphically illustrates the method for calculating an integral value across a selected time portion of a heart signal cycle from a single sensor location.

Referring now to FIG. 1B, ECG data is preferably acquired simultaneously from each sensor 12 of array 10 at a sampling rate of about 500 Hz or more, ideally at a sampling rate of about 1,000 Hz or more. In some embodiments, sequential sampling of sensor 12 from array 10 may alternatively be used, and higher or lower sampling rates are also feasible. Poor quality or absent signals may be visually and/or automatically identified and rejected. Such rejected or absent signals may be replaced using interpolation of adjacent lead recording data. Interpolation and/or filtering techniques may also be utilized to correct for offset variation among electrodes, and for linear baseline drifting.

Graph 14 includes an ECG signal tracing 16 representing the variation in voltage over time, as sensed by sensors 12, optionally at about 1 to 2 ms intervals. Signal tracing 16 may be used to evaluate heart cycle signals from the heart of patient P. In general, one or more reference heart cycles will be selected for manipulation and comparison. The reference heart cycle may be the heart cycle coinciding with initiation of the arrhythmia for focal AFib, or any cycle during VT, for example. ECG Tracing 16 can be used to determine a beginning 18 and end 20 of a time portion 22 of the reference heart signal cycle which is of particular interest for evaluating one or more regions of the heart. In the example illustrated in FIG. 1B, a P wave onset may be determined by the time at which the voltage progresses beyond a predetermined threshold, for example, 30 $\mu$V, while termination of the P wave may be defined at the atrial J-point, as is generally understood in the field of electrocardiography. Alternative criteria for P wave onset and offset might also be utilized, and automated detection of time portion 22 is also feasible. Alternative time portions may also be selected, for example, QRS data may be analyzed for localization of VT.

Referring to FIGS. 1B and 1C, measurements made at each sensor 12 are preferably mapped onto a graphical map or plot 24 of a data matrix according to the locations of the associated sensor. In the exemplary embodiment, a numerical valve of a P wave integral may be calculated based on heart cycle signals 16 within selected time portion 22 for a particular sensor location N10. This calculated P wave integral value reflects the time/amplitude area of ECG signal at that sensor location within the selected time portion. Similar integral values are calculated for each sensor location, and the sensor values are mapped within a data matrix continuously from a portion of the data matrix associated with a front F of torso T, across a side of the patient P, and to a back B portion of torso T. As shown in FIG. 1C, the data matrix will often be presented graphically by calculating lines of constant integral values 28 based on the individual discrete integral values and their associated positions within the data matrix. In some embodiments, this information can be summarized by presenting a single line 30 of zero integral value between a region of positive integral values 32 and a region of negative integral values 34. In much of the description which follows, the region of positive integral values 32 is presented as a shaded region within the graphical map 24 of the data matrix. Exemplary alternative data matrices may be presented with shades of a first color (red, for example) for positive values, a second color (blue, for example) for negative values, and optionally a third color (such as green) for zero.

For localizing of certain arrhythmias (possibly including VTs and some types of atrial tachycardia), directly using measurements from sensors 12 to calculate integral values 26 for the selected time portion 22 may be sufficient to identify an arrhythmogenic region (which may be relatively large) of a particular ventricle, and in some cases, a particular atrium. Localizing directly from the sensed heart cycle signals is significantly facilitated when the signals within the time portion of interest are predominantly indicative of activity within a candidate ectopic region of the heart. For example, when localizing VT, selecting a time portion dominated by the QRS complex in the signal can effectively localize arrhythmogenic foci, as more fully described in the *J. Am. Coll. Cardiol.*, 24:1708–1724 (1994), the full disclosure of which is incorporated herein by reference. This localizing of tachycardia foci within the ventricle may be facilitated by the domination of the QRS complex in the signal of the overall body surface potential.

Unfortunately, when localizing fibrillation foci within an atrium, the P wave (which can be indicative of activity within the atrium) will often be superimposed, either partially or completely, by the T-U wave. Physiologically speaking, the atrial activity of interest may coincide with ventricular recovery of the preceding cardiac cycle. To accurately localize focal triggers during the initiation of paroxysmal atrial fibrillation, the present invention can make use of systems and methods for separating a signal portion of interest from a superimposed signal portion, with the two signal portions often being separated from a single signal sensed from at least one single sensor location. These signal separation techniques are particularly advantageous when used to isolate the P wave from a simultaneously occurring T-U wave. It may be possible in some circumstances to artificially separate these waves by active pacing using an intracardiac catheter with a pacing period selected to avoid superimposition of these two signal portions during artificially initiated arrhythmia. Alternatively, as will be understood with reference to U.S. Provisional Application No. 60/189,611, and also with reference to a provisional application filed on Mar. 15, 2000, entitled "QRST Subtraction using Adaptive Template for Analysis of T Wave Obscured P Wave" (both of which are incorporated herein by reference), a QRST subtraction program can isolate and preserve the P wave morphology so as to enable trigger localization of focal AFib and other arrhythmias. The application of similar subtraction methodologies may also enhance the ability of body surface mapping systems to localize other sites of interest for diagnosing or treating arrhythmias, such as the ectopic origin of rapid atrial tachycardia with 1:1 atrio-ventricular conduction and the atrial insertion site of a concealed accessory pathway or to isolate atrial flutter.

Figure 2:
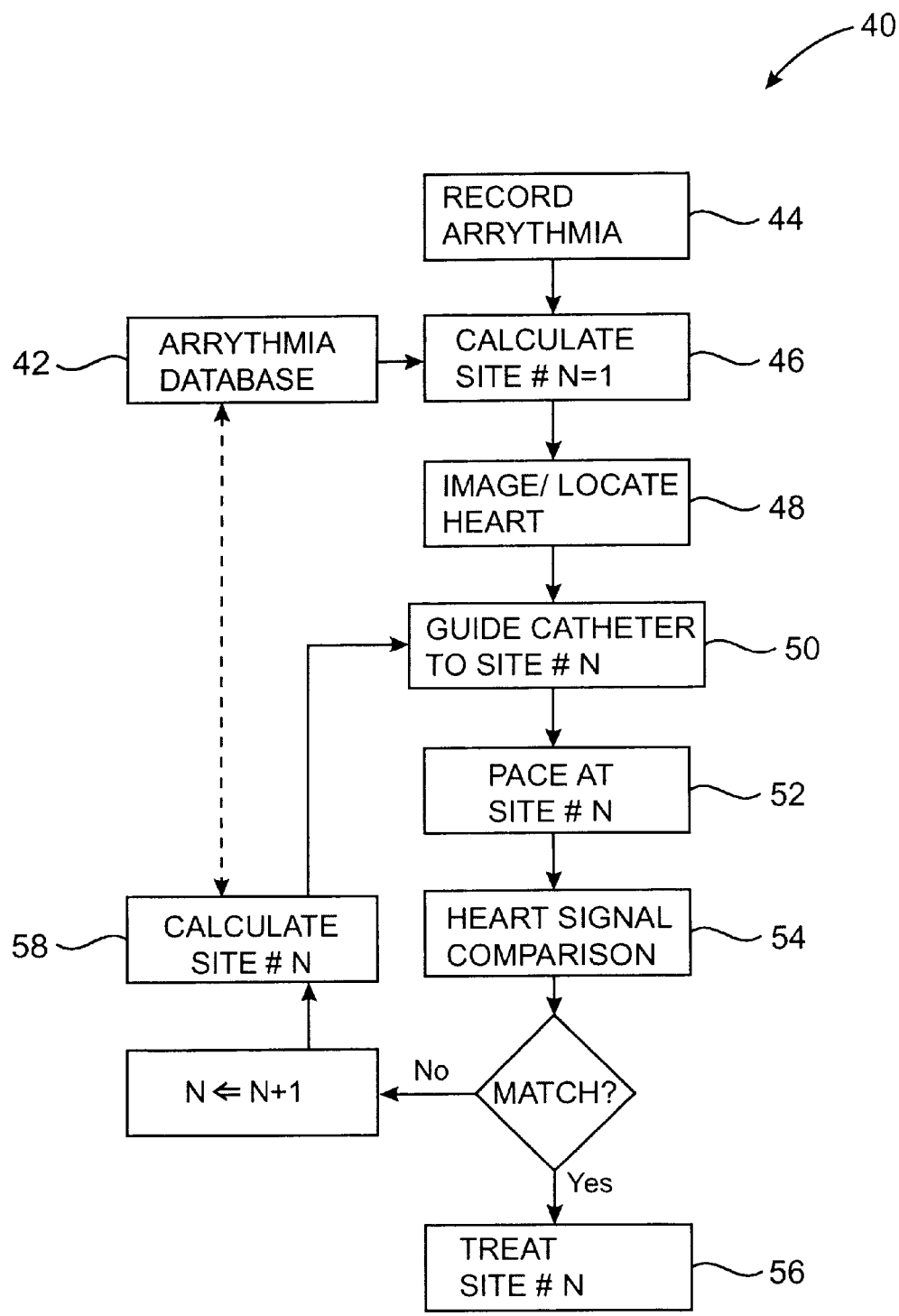
FIG. 2 schematically illustrates a method and computer program for localizing an ectopic or exit site, either absolutely (using a pre-established database) and/or relatively (based at least in part on measurements previously taken from the patient).

Referring now to FIG. 2 an exemplary localization and treatment method 40 will often make use of a pre-existing arrhythmia database 42, the arrhythmia database typically including mean paced maps taken from a variety of individuals at multiple pacing locations, as will be described hereinbelow. When seeking to localize an arrhythmia for a particular patient, heart signals of the arrhythmia for the patient will be captured and recorded 44, preferably using array 10 as described above. The recorded heart signals will often be manipulated as described above to generate one or more integral data matrix and/or plot.

Statistical comparisons of the recorded arrhythmia 44 to the database 42 will often allow calculation 46 of a candidate ectopic or exit site. The initial calculation may be performed using only surface measurements taken from the patient's body surface and the database of previous patient morphologies and associated pacing sites. Use of these external sources of information is generally referred to as "absolute" localization. Alternatively, related methods may be used after initiation of pacing, optionally being based entirely on data from the patient.

It will often be beneficial to accurately identify the location of diagnostic and/or treatment structures (such as a pacing catheter electrode) relative to one or more tissues within the heart, particularly while imaging the heart tissue in three dimensions, for example, using biplane fluoroscopy in an electrophysiology lab. To help establish the location, orientation, and/or dimensions of a heart chamber of interest, anatomical locations in space or datum points may be identified in step 48. In the exemplary embodiment, this information is used to graphically indicate or superimpose the calculated candidate site on the displayed tissue image so as to help guide a diagnosing and/or treatment catheter toward the candidate site 50.

Where further refinement in the localization is desired, the catheter may pace at the candidate site 52 while measurements are taken by sensor array 10. Heart signals measured by the array during pacing may be compared to the heart signals from the original arrhythmia 54. If the paced heart signals match the recorded arrhythmia, the site may be treated 56, using either the same or a different catheter.

If the heart signals obtained by pacing at the candidate site do not match the recorded arrhythmia within a desired tolerance, a new candidate site 58 may be calculated. Optionally, the new candidate site may be calculated by determining an adjustment vector or function. Such specific guiding to one or more sequential pacing sites can significantly decrease the total number of pacing sites required. In some embodiments, this may involve calculating an estimated pacing location from the paced heart signals. The estimated pacing location may be compared to an actual pacing location, which may be determined using a frame grabber and image analysis system coupled to the biplane fluoroscopy to calculate a three dimensional position of a radio-opaque marker (such as an electrode) of the catheter. Alternatively, known magnetic catheter location systems, electrical location systems, ultrasound location systems, or the like might be used. The adjustment vector or offset may then be applied to the calculated candidate site. Optionally, the pacing location and measured heart signals may be added to the database. When sufficient specific information from this patient is available (for example, when three or more pacing locations and associated integral maps have been obtained), the entire database may be specific to the patient undergoing diagnosis or treatment.

Localization which makes use of patient-specific pacing location and heart signal information is sometimes referred to as "relative" localization. In many embodiments, relative localization will have significant accuracy advantages, particularly when a plurality of pacing locations have been captured. Eventually, when sufficient relative localization accuracy has been achieved, the recorded arrhythmia and paced heart signal will match and treatment can be initiated. Advantageously, the localization system may graphically guide a pacing/ablation catheter to successive candidate sites by superimposing the calculated candidate site with the imaged heart tissue and catheter, ideally in three-dimensions, significantly facilitating the procedure.

Figure 3:
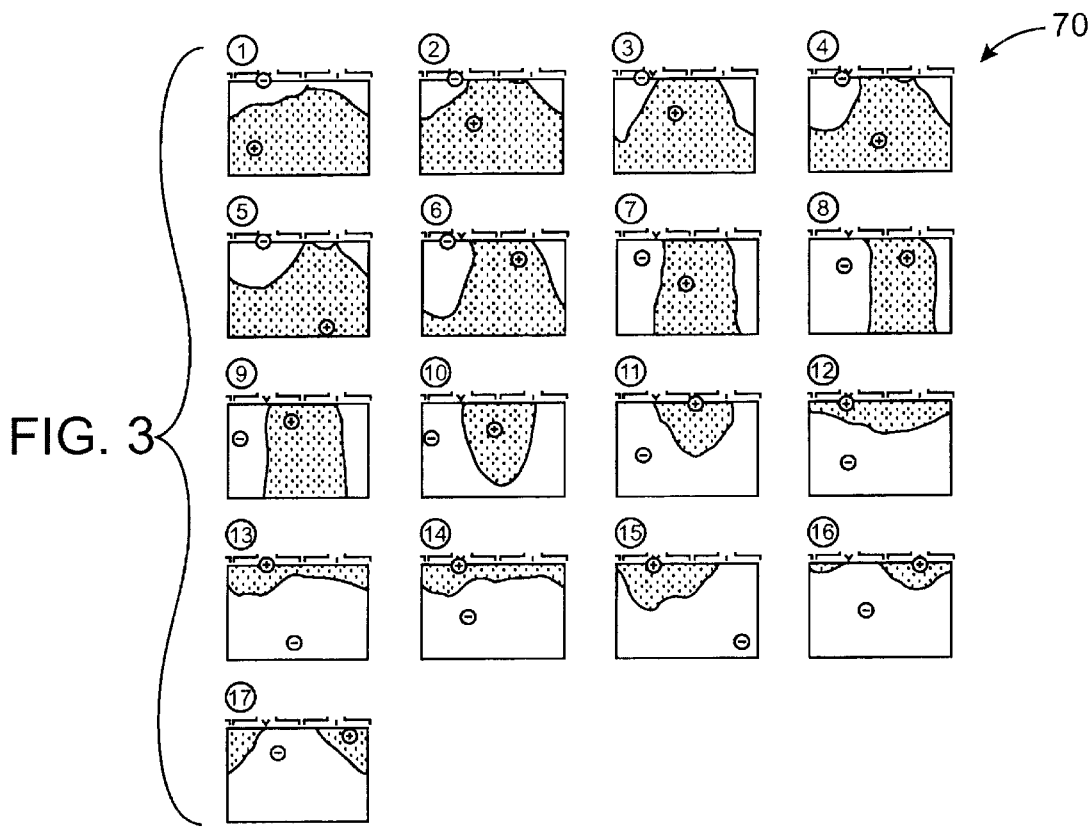
FIG. 3 graphically illustrates a database of known atrial paced heart cycles as 17 mean P wave integral maps.
Figure 4:
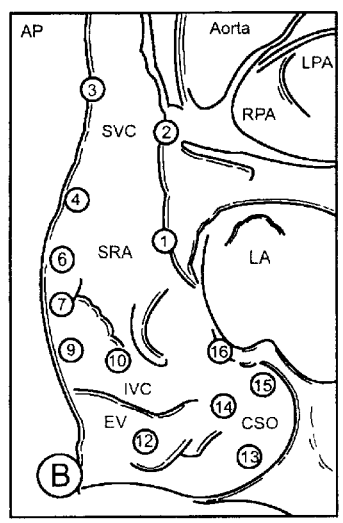
FIGS. 4 and 5 illustrate 17 known right atrial ectopic origins associated with the 17 mean P wave integral maps of FIG. 3.
Figure 5:
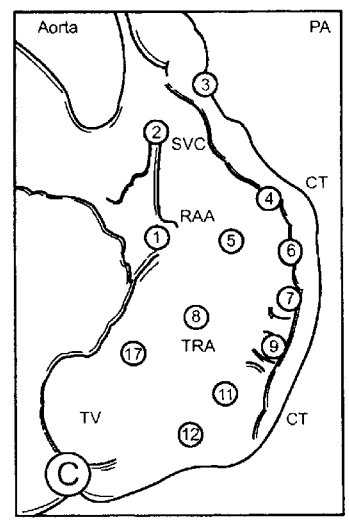
Figure 6:
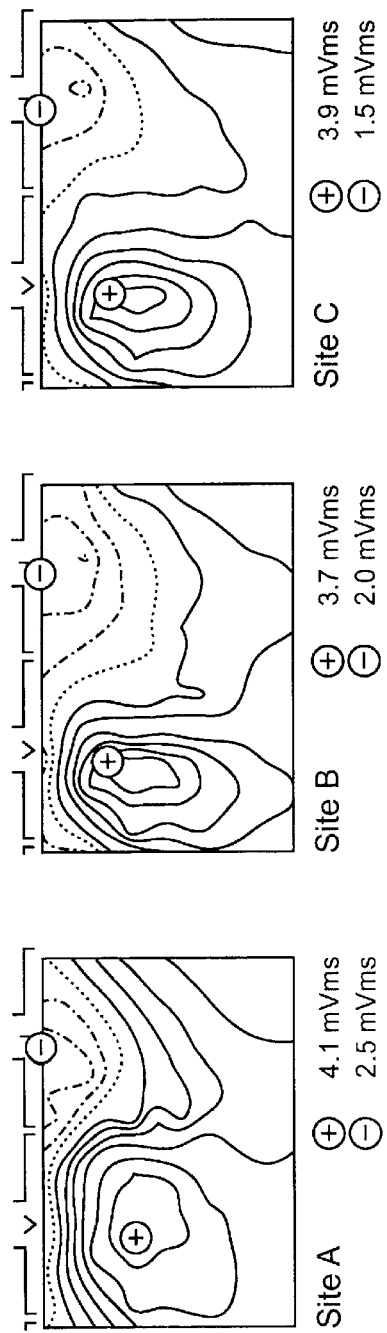
FIGS. 6A–F illustrate correlations between integral maps of arrhythmias within a common arrhythmogenic region.

Referring now to FIGS. 3–5, a graphical plot of a particular patient's P wave integral may be used to localize an arrhythmogenic region in an atrium by comparing the P wave integral plot for the patient to a database of P wave integral plots having associated known ectopic foci within the right atrium. Each of the 17 plots of database 70 has an associated ectopic region (identified by the encircled numbers illustrated in FIGS. 4 and 5).

The anterior-posterior view AP shown in FIG. 4 and the posterior-anterior view PA of FIG. 5 illustrate the right atrial cavity. Anatomical landmarks included in these diagrams include the superior vena cava SVC and inferior vena cava IVC; the right atrial appendage RAA; the smooth right atrium SRA; the trabeculated right atrium TRA; the crista terminalis CT; the fossa ovalis FO; the left atrium LA; the Eustachian valve EV; the coronary sinus os CSO; the tricuspid valve TV; the right pulmonary artery RPA; and the left pulmonary artery LPA.

Methods For Assembling A Right Atrial Database are described in detail in the J. Electrocardiol., 31 (Supp.) :85–91 (1998), incorporated herein by reference. The mean P wave integral maps of atrial database 70 feature extreme positions and zero line contours without positive and negative integral contour lines. Alternative plot formats, such as three-dimensional or chest anatomy-based formats, map displays using various color schemes, and the like, may also be used. A similar left atrial database may be prepared using a trans-septal or retrograde aortic approach, with each database again benefiting from accurate information regarding the positioning of the pacing catheter, as described above and as described in more detail in a provisional application filed on Apr. 11, 2000 and entitled "Database of Body Surface ECG P Wave Integral Maps for Localization of Leftsided Atrial Arrhythmias," the full disclosure of which is incorporated herein by reference.

These databases have generally been prepared by grouping together sets of pacing data having similar morphologies and pacing locations from a number of tests. Each of the mean paced maps of the databases and the associated known ectopic or exit sites or regions has been assembled from a series of individual pacing tests on several different patients. Referring now to FIGS. 6A–F, six individual P wave integral maps included within a group were each obtained during pacing at the left upper and left lower pulmonary veins of the left atrium. These six similarly located pacing sites were grouped together within a single group of a left atrial database, and these plots were averaged to produce one of the mean plot of the left atrial database. The spatial or morphological compatibility of these patterns can be clearly seen, particularly with reference to the location and orientations of both the highest positive and negative integral values, as well as with reference to the zero line contour separating the shaded from unshaded regions. While each of these six patient-specific maps were generated using intra-cardiac pacing, naturally occurring ectopic origins may be identified by comparing reference heart cycle signals measured during atrial tachycardia or the onset of atrial fibrillation (and optionally separated from superimposed signals as described above) to the mean paced plots of the database.

Figure 7:
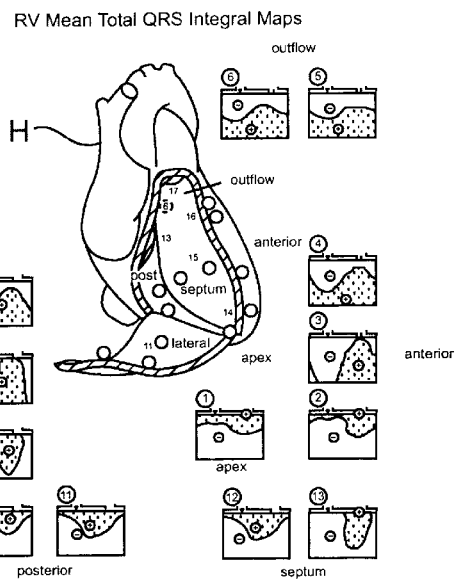
FIG. 7 illustrates a database of QRS integral maps and associated ectopic origins within the right ventricle.
Figure 8:
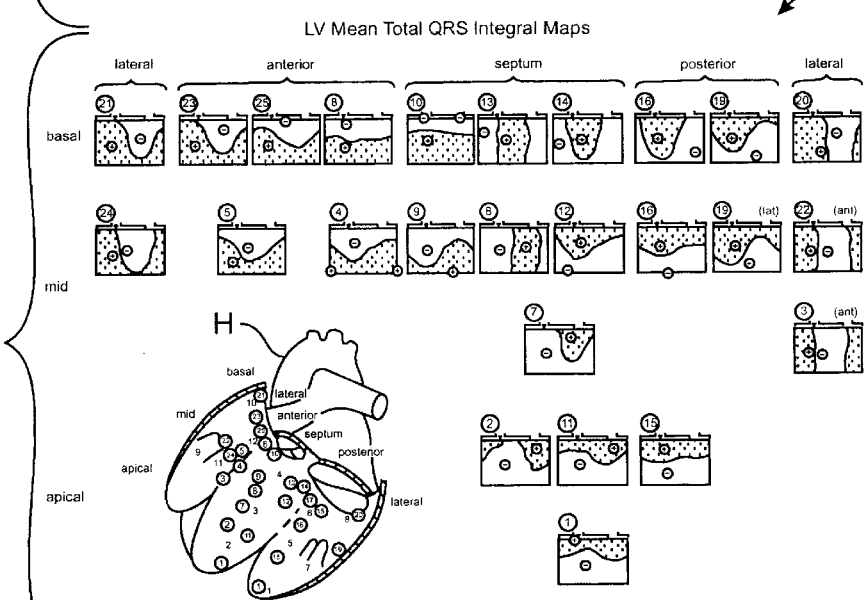
FIG. 8 illustrates a database of QRS integral maps and associated ectopic origins within the left ventricle.

Referring now to FIGS. 7 and 8, a right ventricular database 82 and a left ventricular database 84 each include mean QRS integral maps for paced ectopic origins in the right and left ventricles, respectively. These ventricular databases are more fully described in an article by Heidi A. P. Peeters, et al. entitled "*Clinical Application of an Integrated 3-Phase Mapping Technique for Localization of the Site of Origin of Idiopathic Ventricular Tachycardia,*" *Circulation* 99:1300–1311 (1999) the disclosure of which is incorporated herein by reference.

FIGS. 9A–D illustrate panels 4A–D, respectively, which include powered components for use in a high noise environment (this panel system sometimes being called an active panel system). Describing the structure of panels 4 using the exemplary panel 4A illustrated in FIG. 9A, the panels generally comprise a thin, planar, and flexible (but often not elastic) polymer film substrate 60. Substrate 60 has an axially length L and a lateral width W suitable for supporting most and/or all of the sensors 12 to be mounted on a quadrant of the patient's torso for localization of an arrhythmia. Sensors 12 will generally define an at least two-dimensional panel array on each panel. More specifically, the sensors will typically define a two-dimensional array when a flexible panel is maintained in a planar configuration prior to mounting on the torso), and will define a three-dimensional array once the panel is in a curved configuration such as when the panel is mounted on the torso for use. Preferably, at least seven sensors will be supported by each panel 4. Electrically conductive leads 62 extend from each sensor 12 to a connector 65 for coupling of panel 4A to analyzer 6. Leads 62 may be defined by selectively depositing a conductive material onto substrate 60, and/or by selectively removing portions of a conductive layer applied across substrate 60 using known circuit fabrication techniques.

Selected displaceable sensors 12a included on panel 4A are adapted for lateral displacement from an initial lead position, often for coupling to a patient's body surface beyond the perimeter of the panel. Deflectable lead support filaments 64 facilitate lateral displacement of displaceable leads 12a. More specifically, cut outs 66 through panel 60 define elongate and optionally, serpentine lead supporting filaments of panel material. Electrical leads extending along these filaments maintain electrical coupling of displaceable sensors 12a with connector 65 when sensors 12a are moved from within the panel perimeter and attached to the patient's body surface along, for example, a shoulder or arm, a leg, or the like.

Selective cutouts 66 through panel 60 may also define means for accessing at least some of the standard ECG lead placements 68. These accessing means act as guides to help position some or all of the 12 standard ECG leads, allowing panels 4 to be used in conjunction with known 12-lead ECG analysis systems, and/or with improved 12-lead systems which may become available in the future.

Panels 4 may also include alternative structures for accessing the standard 12-lead sensor locations. For example, sensors 12 may be supported by panel 4A at one or more standard locations, with take-off connectors or "snaps" for transmitting signals from the standard sensor locations to alternative ECG analysis devices provided either on the standard location sensors, or anywhere across the panel. Still further alternatives include a data transmission output from analyzer 6 or directly from the panels for transmitting the standard ECG sensor information. Many of these options will allow analyzer 6 as well as the alternative ECG data analysis system to make use of the standard ECG information, avoiding any need to interpolate the standard information or combine data from a separate ECG system with data from array 10.

As has previously been mentioned, panels 4 may be optionally used in combination with a medical imaging system such as a magnetic resonance imaging system, an ultrasound imaging system, a fluoroscopy system, or the like. In the exemplary embodiment, biplane fluoroscopy will be used to provide three-dimensional imaging of at least a portion of the heart while measuring heart signals during intracardiac pacing or direct catheter-based mapping of an arrhythmia. To avoid degradation of image quality, panels 4 will often include one or more windows 70, with the windows generally being significantly more transparent to a desired imaging modality than at least a portion of the panel beyond the windows.

To enhance image quality, sensors 12b within window 70 maybe be adapted to have a greater transparency than at least some of the sensors disposed beyond the window. For example, some of the sensors disposed beyond window 70 may include a metallic electrode, such as a silver/silver chloride electrode, while sensors 12b within window 70 may comprise a non-metallic electrode such as a carbon electrode, or a metallically impregnated carbon electrode with a sufficiently low metal content so that the electrode is functionally transparent for imaging. Suitable carbon electrodes include those described by Arne SippensGroenewegen, et al. in "*A Radiotransparent Carbon Electrode Array for Body Surface Mapping During Cardiac Catheterization*", *Proceedings of the 9th Annual Conference of IEEE Engineering in Medicine and Biology Society*, New York: IEEE Publishing Services, pages 178–181 (1987), previously incorporated herein by reference. Similarly, leads 62 within window 70 may comprise a non-metallic material such as carbon, while at least some of the electrical connection between sensors 12 and analyzer 6 beyond window 70 can optionally make use of metallic structures. Shielded leads may also be used to improve signal quality.

In addition to using radiotransparent materials (or materials which are otherwise transparent or nearly transparent to a desired imaging modality) within window 70, components of panels 4A that are deleterious to image quality may be positioned beyond a perimeter of the window. As will be described in detail herein, powered circuits may be distributed among sensors 12 to improve sensor signal quality. As such powered circuits may include image degrading components, these power circuits will often be positioned on substrate 60 outside of windows 70.

As panels 4 may be used to sense heart signals during paced and other arrhythmias, it may be desirable to electrically cardiovert and/or defibrillate (or otherwise stimulate) the heart of the patient to establish a regular heart beat at some time during the use of panels 4, and optionally repeatedly while arrhythmias are being evaluated. To avoid having to resort to repeatedly removing or displacing some or all of sensors 12 to apply external defibrillation electrodes, panels 4 may include one or more integrated heart stimulation structures such as external stimulation electrodes 72. Heart stimulation electrodes 72 will often have an outer perimeter 74 extending around one or more of the sensors 12. To avoid signal contamination and/or damage to the signal sensing system, an opening 76 within simulation electrode 72 around the sensor (and its lead) helps to maintain electrical isolation between the sensor and stimulation electrode. Opening 76 may also extend to perimeter 74 to facilitate coupling of the sensor via its lead 62 to the associated circuitry of panels 4. A lead 62 capable of handling the desired cardiac stimulation energy may connect stimulation electrode 72 to connector 65, or an independent stimulation electrode connector may be provided, optionally adjacent to the stimulation electrode along the panel. In the exemplary embodiment standard defibrillation connectors and discrete wires (in contrast to the panel-supported flex leads 62) transmit power to the defibrillation electrodes to better withstand the higher voltage and current involved in heart stimulation.

Stimulation electrode 72 may optionally extend into window 70, with the stimulation electrode material disposed within the window preferably comprising a material which is sufficiently transparent to the desired imaging modality to provide a desired image. For example, stimulation electrode 72 may comprise carbon filaments coupled to the patient's torso by an electrically conductive gel. Stimulation electrode 72 may also have a structure similar to electrodes 12 but with a large surface area. In some embodiments, stimulation electrode 72 may extend into openings 66, with the electrode structure being supported by a separate defibrillation electrode support.

Figure 9A:
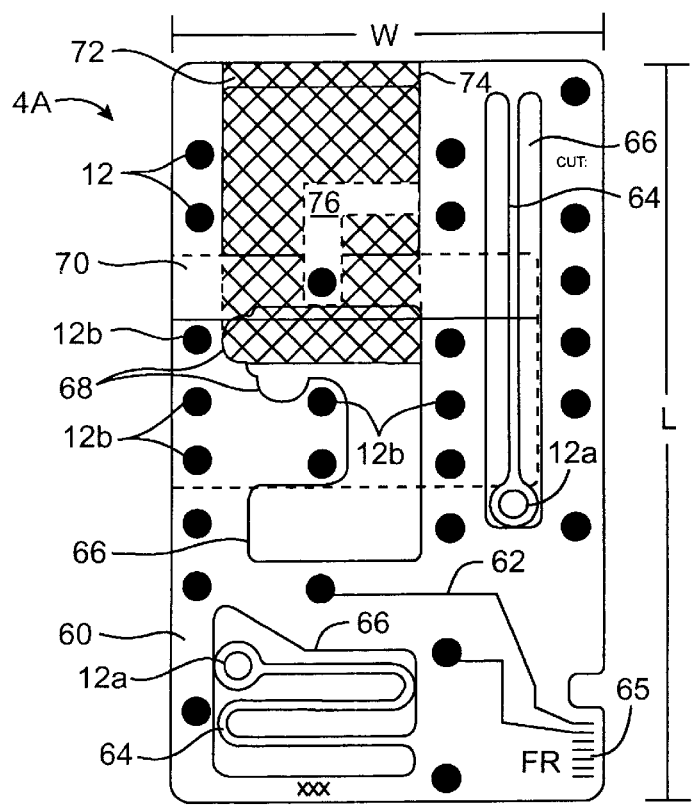
FIGS. 9A–D illustrate the four panels of an exemplary four panel array system.
Figure 9B:
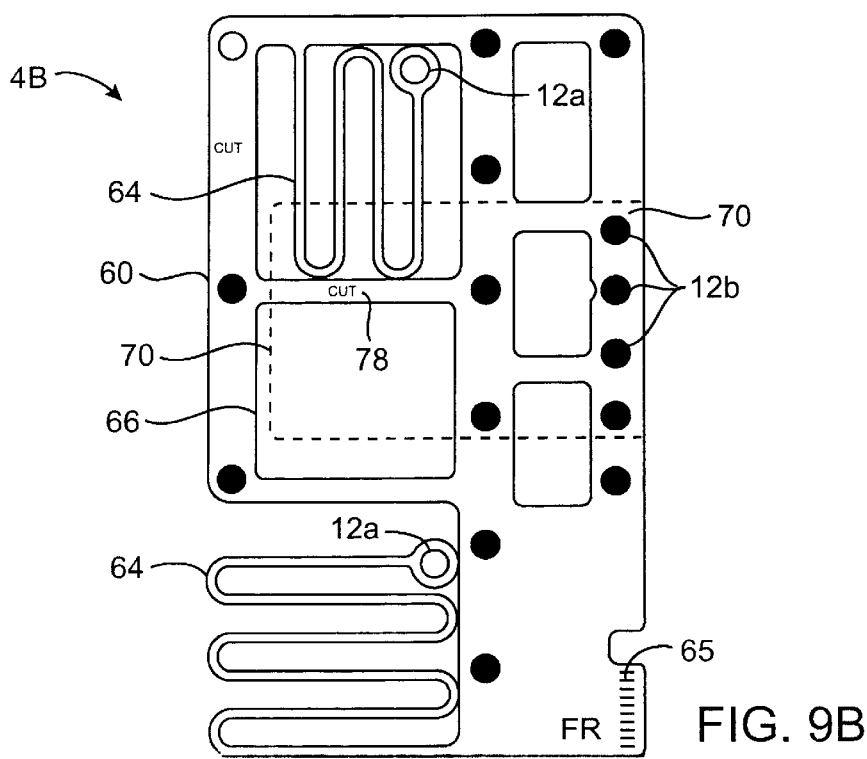
Figure 9C:
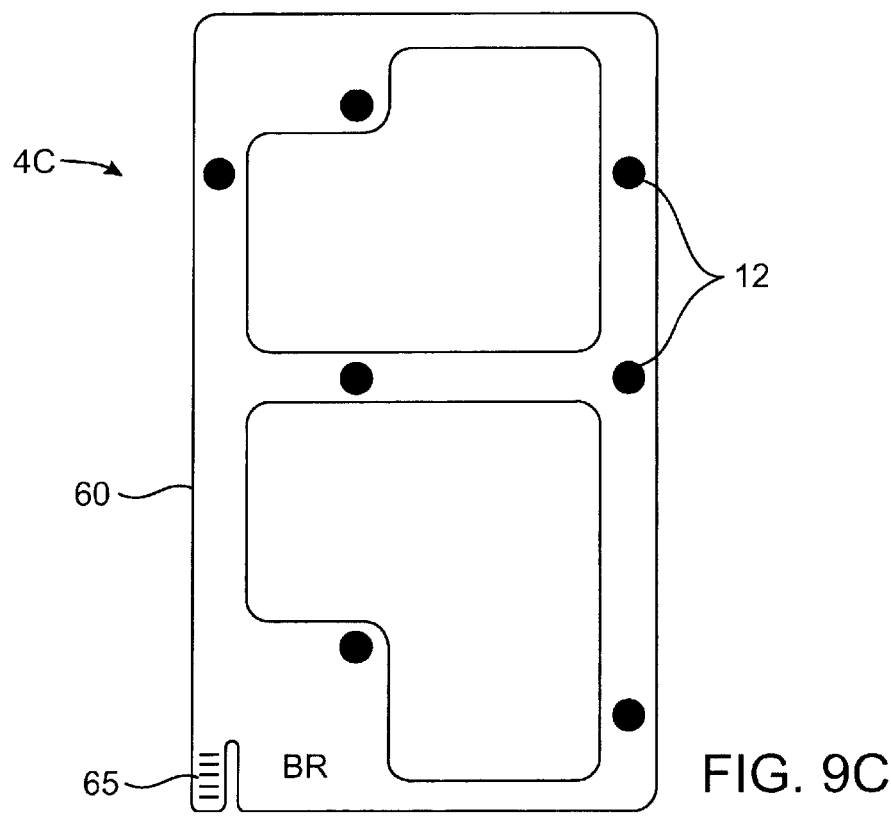

In the exemplary embodiment, the four panels 4A–D are each adapted to support sensors 12 in appropriate engagement with an associated quadrant of torso T. Advantageously, individual mounting of panels 4 on torso T allows some adjustment for patients having differing external anatomy. Lateral width of torsos vary to a greater extent than inferior/superior length of the torso, and separating the torso into circumferential quadrants allows the multiple panel structure to be positioned with selective spacing between the panels to accommodate these differences. Nonetheless, as patients will vary significantly in height, a modest number of alternative panel sizes may be provided, with the physician selecting the panel size suitable for the patient. Two to ten different sizes of multi-panel systems may be sufficient to cover at least most patient sizes. Openings 66 through panel substrate 60 generally increase the adaptability of panels 4 to varying external anatomies, particularly where the openings define severable cross-members 78, as shown in FIG. 9B.

The use of an inelastic flexible substrate 60 generally enhances the alignment rigidity or placement accuracy of sensors 12. Nonetheless, panels 4 will benefit from differing configurations for differing external anatomies. For example, although rigidity in lateral positioning of the sensors across the chest is generally desirable, selective detachment of severable cross-members 78 may accommodate breasts, differences in musculature, weight, and other variations within patients of the same general size. To facilitate changes in configuration of panels 4, leads 62 will often extend around severable cross-members 78 along alternative portions of substrate 60.

Figure 9D:
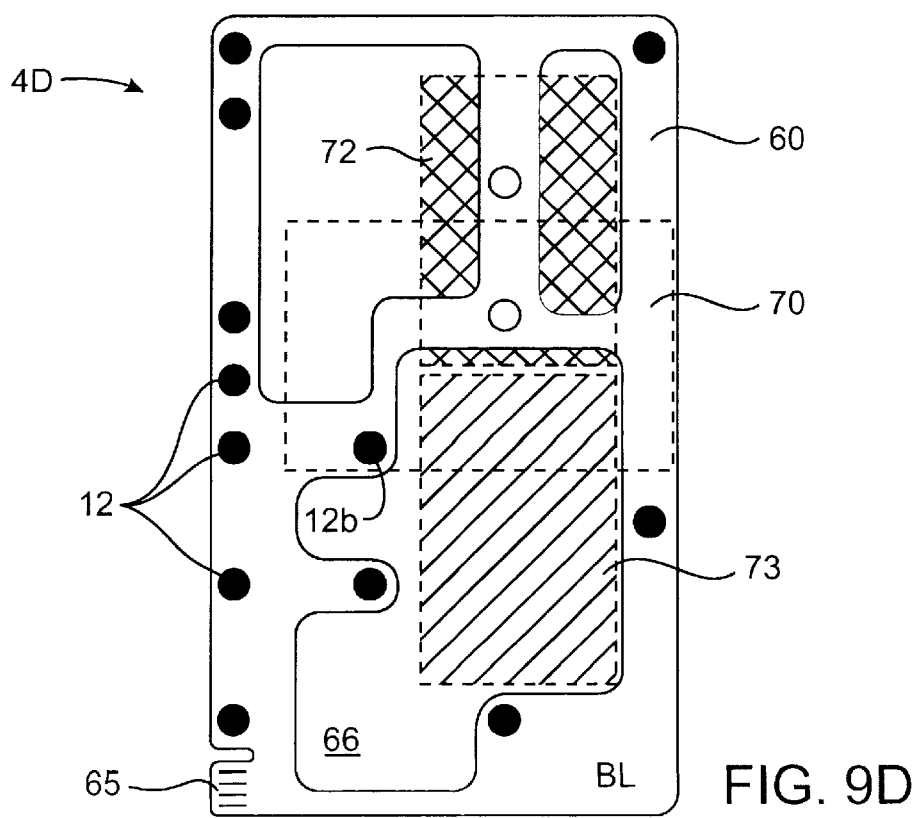
Figure 19:
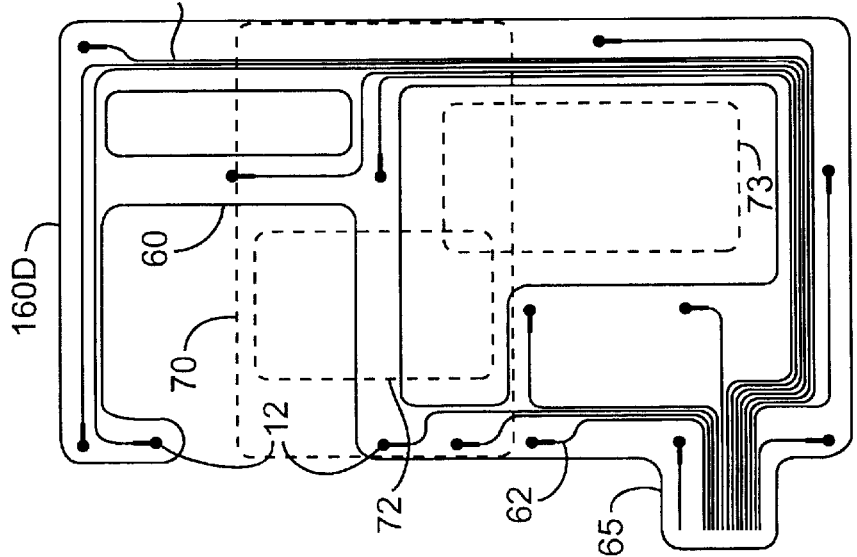
Figure 20:
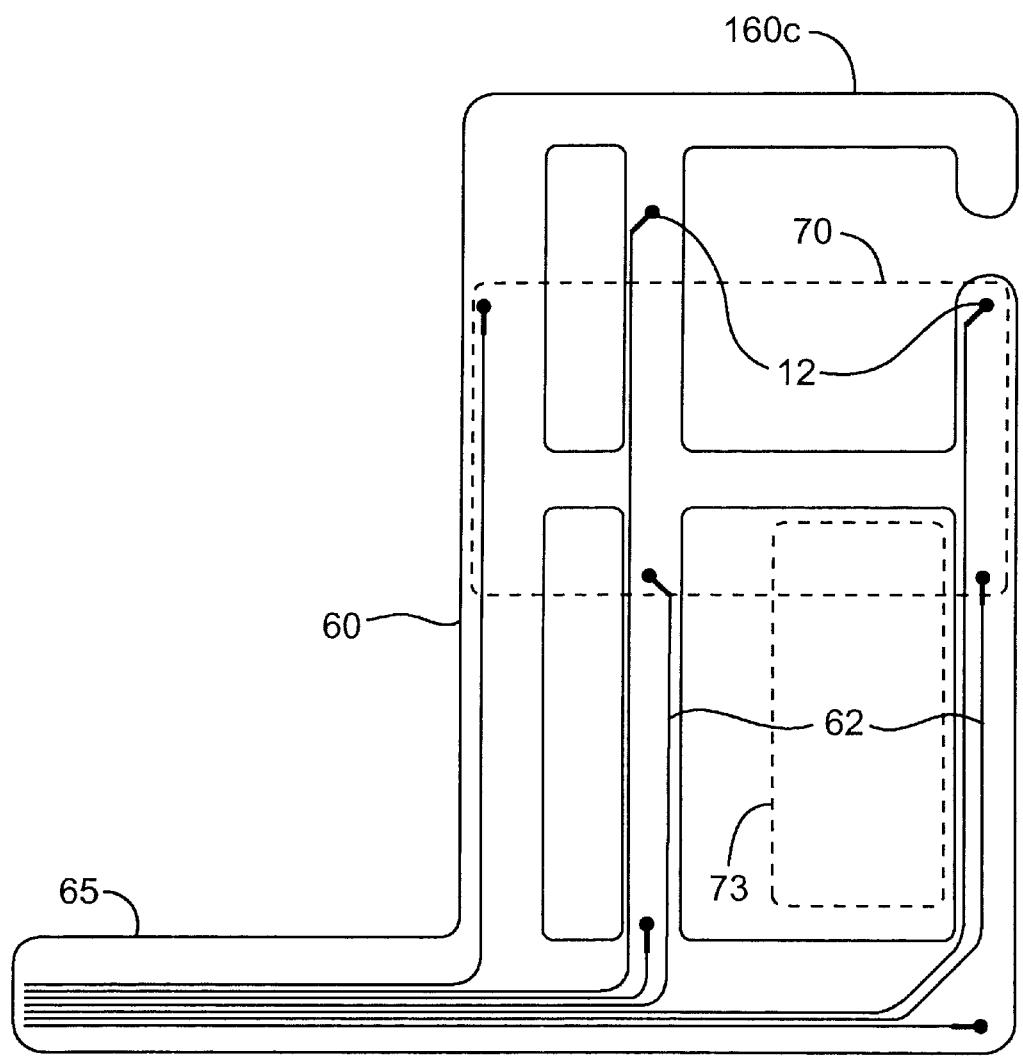

Still further structures may be incorporated within panels 4. For example, intracardiac ablation catheters often make use of a large "indifferent" return electrode coupled to a patient's back or thigh so as to complete a circuit. These ablation catheters may comprise quadripolar structures, in which current transmitted from the tip electrode to the return electrode is used for ablation, and in which two bipolar pairs can be used for recording or stimulation. A return electrode 73 may be readily accommodated on at least one panel, preferably in a posterior panel structure, as shown in FIGS. 9D, 19, and 20.

As can be understood with reference to FIGS. 1, 9A–D, and 20, leads 62, connector 65, and cables 8 will preferably be arranged along both the front and back of the patient so as to extend laterally toward a common side of the patient, for example, toward the patient's left. This improves physician access to the patient via the patient's right side when panels 4 are coupled to analyzer 6.

Referring once again to FIG. 2, initial recording of an arrhythmia may take place in a relatively low-noise environment (as compared to an electrophysiology lab). Hence, the initial arrhythmia recording may make use of a lower cost panel system which lacks these high-noise components and capabilities. Although the exemplary panel structure illustrated in FIGS. 9A–D include several features which provide significant capabilities at a reasonable cost, it may be desirable to provide alternative sensing systems at a lower cost, particularly for use when a noisy environment (such as an electrophysiology lab) can be avoided. Such noisy environments benefit from the distribution of powered circuits among the electrodes, as well as from the specialized defibrillation electrode structures, imaging windows, return or "indifferent" electrodes, and other cost-increasing components of panels 4.

Referring now to FIGS. 10A through 11D, the electrical components and structure of the panels 4 are shown in more detail. As seen most clearly in FIGS. 10A and 10B, a surface 86 (sometimes referred to as an inner surface or tissue-engaging surface) of substrate 60 is generally adapted to affix panel 4 to the torso surface. More specifically, an adhesive impregnated foam 88 may be disposed along tissue engaging surface 86 around an electrode body 90 of sensor 12. Alternatively, the electrode gel may provide sufficient support without an adhesive foam. Electrode body 90 will be electrically coupled to the torso surface by removing a peel-away polymer sheet 92 from substrate 60 so as to expose adhesive foam 88, and engaging the adhesive foam (and an electrically conductive gel or adhesive 94 surrounded by the foam) against the patient's skin. Conductive gel or adhesive 94 provides electrical communication between the patient's skin and electrode body 90.

Substrate 60 may comprise a variety of materials, such as rubber, fabric, polyester, polycarbonate, polystyrene, and other polymer materials, such as Kapton™ polymers. The substrate will often have a thickness in a range from about 0.005" to about 0.07". Electrode body 90 may comprise metallic (such as silver/silver chloride, platinum, silver, gold, and the like) or non-metallic (such as carbon) materials. Leads 62 will preferably comprise a conductor deposited on substrate 60 as an ink, with the leads generally maintaining continuity when the substrates flex. Suitable conductive inks may include carbon, carbon/silver blends, silver, silver/silver chloride, gold, platinum, copper, UV cured dielectric materials, heat cured dielectric materials, or the like. Suitable conductive lead inks may be commercially available from Acheson®, Ercon®, Creative Materials®, and other ink manufacturers. Leads 62 will typically comprise features having a width of at least about 0.010", with gaps of at least 0.015" between separated features. Adhesive foam and electrolytic gels may be commercially available from a variety of suppliers. A non-metallic (carbon-based) adhesive may be available Adhesive Research™. A variety of conductive panel fabrication services may be commercially available for manufacturing of panels 4, including services provided by Conductive Technologies of York, Pa.

Figure 10A:
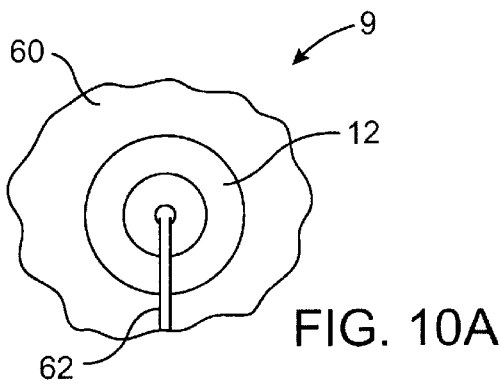
FIG. 10A is a top view of an electrode of the array.
Figure 10B:
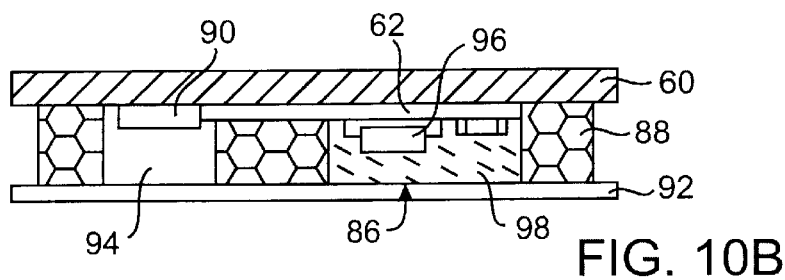
FIG. 10B is a cross-section showing an electrode of one of the four flexible panels.
Figure 11A:
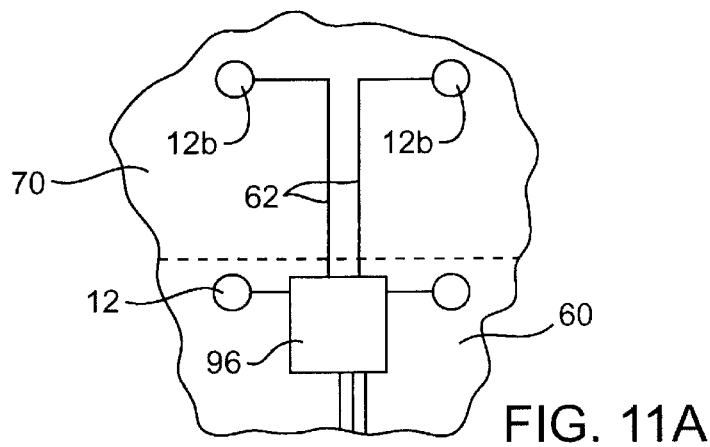

As can be understood with reference to FIGS. 10B and 11A, powered circuits 96 will often be distributed among sensors 12 of the array. Locating such powered circuits in close proximity to (and optionally on top of) to sensors 12 dramatically improves the signal gathering performance of the array, primarily by reducing the electronic and magnetic noise. Such noise is particularly problematic in the high-noise environment of an electrophysiology lab, in which mains power (at 50–60 Hz) is flowing, in which therapeutic RF electrical energy will often be available and/or in use, in which fluoroscopy and other imaging modalities may be required for certain procedures, and the like.

Figure 11B:
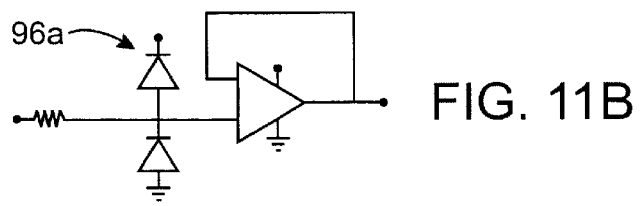
Figure 11C:
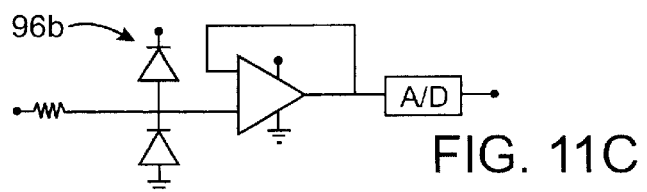

Powered circuits 96 may provide amplification, buffering (strengthening the drive of signals sensed by sensor 12 to help transmit the signals down the leads to analyzer 6), noise filtering, analog-to-digital conversion, electrical-to-optical conversion, and/or the like. In preferred embodiments, some or all of these functions may be preferred by transmitter 3 as shown in FIG. 1. To provide one or more of these capabilities, powered circuits 96 will generally have three or more leads extending therefrom, with power being supplied by a difference in potential between at least two of the leads. A simplified amplifier powered circuit 96A is illustrated in FIG. 11B, while a simplified analog-to-digital converting powered circuit 96B is illustrated in FIG. 11C.

In some embodiments, one or more of the sensors 12 may have powered circuits 96 co-located with, and dedicated to, a particular sensor 12. Circuit components may be disposed within a protective structure 98 of hardened polymer deposited over and/or adjacent, electrode body 90, the protective structure sometimes referred as a "glop-top". Protective structure 98 adds structural rigidity as well as voltage isolation. Such rigidity helps maintain electrical continuity between the electrical components and leads 62.

Figure 11D:
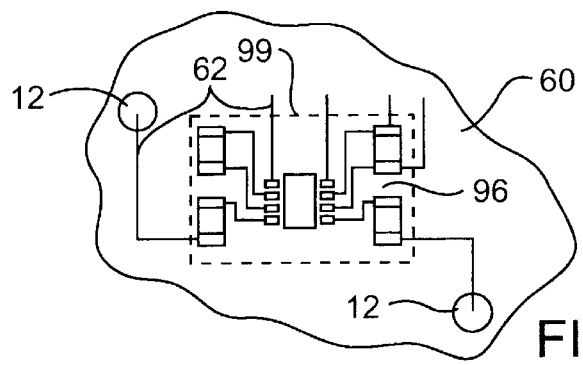
Figure 17:
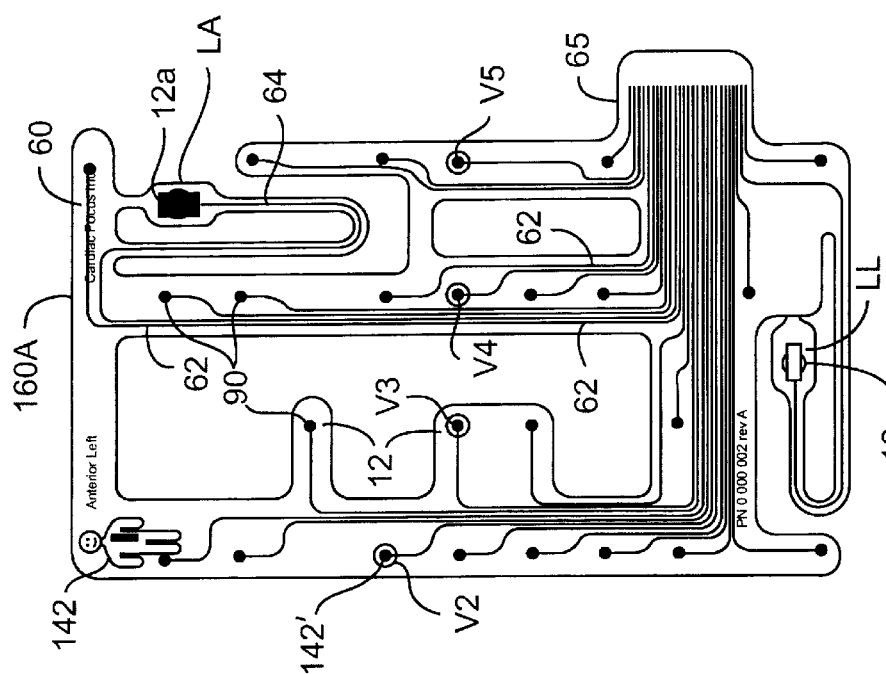
FIG. 17 shows an exemplary substrate with electrodes and lead deposited thereon for use in an anterior left panel of a passive vest structure adapted for use in a low-noise environment.

In many embodiments, powered circuit 96 will pre-process signals from a plurality of sensors 12, powered circuits 96 often amplifying (and/or otherwise improving the transmissibility of) signals for 2, 4, or 8 sensors. As illustrated in FIG. 11A and described above, powered circuits 96 will often be disposed outside of imaging windows 70 so as to avoid degrading imaging quality. Components of an exemplary powered circuit 96 for processing signals from 2 nearby sensors 12 are illustrated in FIG. 11D. Note that powered circuits 96 may comprise a rigid circuit board 99 mounted on flexible substrate 60, the circuit boards coupled to sensors 12, and (connector 65, see FIG. 17) by leads 62.

Figure 12:
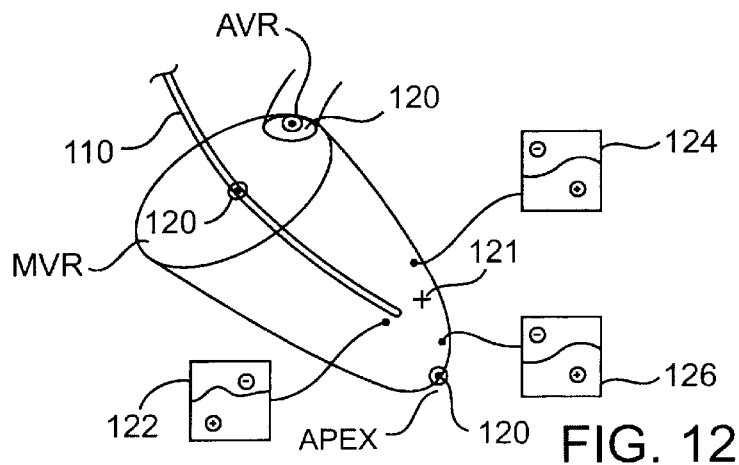
FIGS. 12 and 13 schematically illustrate methods for locating a position and/or orientation of a chamber of a heart in space, and also schematically illustrate relative localization using information obtained from a particular patient.

Referring now to FIG. 12, and as was described above with reference to FIG. 2, it will often be beneficial to identify a location and orientation of the endocardial surface of a chamber of the heart, particularly when a system is intended to guide a catheter toward a candidate site. Additionally, size information regarding the chamber may be used to apply normalized data to the specific patient. Advantageously, pacing and/or ablation catheter 110 may be used to identify datum locations 120 so as to indicate to the system the general layout of the heart chamber. For example, by identifying a center or perimeter of a mitral valve ring MVR, an apex, and a center of an aortic valve ring AVR, often by sequentially positioning catheter 110 at these anatomic structures and taking catheter location measurements at each location, the basic geometry of the patient's heart chamber can be readily modeled by the system.

Referring to FIGS. 12–14B, based on a calculated candidate site and the chamber geometry, the system may generate one or mores sequential graphical position indications 121 to help guide the physician during positioning of catheter 110. The graphical candidate site indicator (or guide) 121 will be revised after each sequential paced map 122, 124, 126 is obtained. Initially, the information included in each paced map may be used in combination with a general database (although even initially it may be used independent of any external database). As more and more patient-specific information is obtained, guide marker 121 should more and more accurately approximate the actual ectopic or exit site. Once sufficient patient/specific information has been obtained, that information may optionally be used independent of any database (if a general database was initially used).

Figure 13:
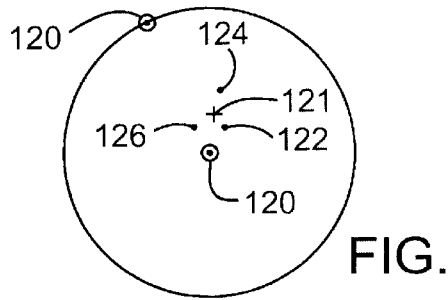
Figure 14A:
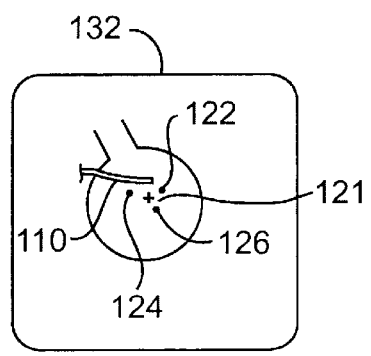
FIGS. 14A and 14B schematically illustrate biplane three-dimensional guided positioning of a catheter for diagnosis and/or treatment of an arrhythmia.
Figure 14B:
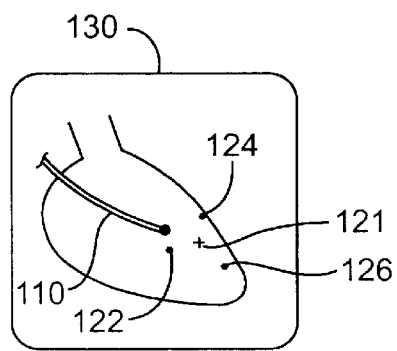

Preferably, guide 121 will provide a three-dimensional position indication, such as by providing separate markers on a right anterior oblique angled fluoroscopic display 130 illustrated in FIG. 14B, and on a left anterior oblique angled display 132 illustrated in FIG. 14A. A variety of other projections and imaging modalities can also be used. Such a three-dimensional guide is particularly advantageous when superimposed on an image of the heart tissue and the catheter 110, as it allows the attending physician to position the catheter with reference to the tissue image and guide. FIG. 13 shows yet another useful graphical representation of positioning within a heart chamber, in which a polar image extends from a chamber apex radially outwardly to a mitral valve ring MVR.

Once an ectopic origin or exit site has been sufficiently localized, ablation of the ectopic origin or exit site is effected, often using an ablation electrode of pacing catheter 110. A variety of alternative tissue treatment modalities might be applied to the ectopic origin, including RF ablation, cryogenic cooling, ultrasound, laser, microwave, bioactive agents, and the like. Similarly, a variety of intra-cardiac localization techniques might be used in place of intracardiac pace mapping under fluoroscopy. Suitable three-dimensional electro-anatomical point-by-point mapping systems may be commercially available for localization of an ectopic origin or exit site from Biosense-Webster, Inc. under the trademark CARTO®, and a related Real-Time Position Management™ system may be available from Cardiac Pathways Corporation of California. An electrical localization system may be available from Medtronic under the trademark Localisa™. Alternative multi-electrode catheters may be commercially available from Cardima, Inc., Biosense-Webster, Inc., Cardiac Pathways, Inc., Bard, Inc. and/or Ep Technologies, Inc. A still further alternative for localizing of the ectopic origin or exit site maybe provided using a three-dimensional non-contact multi-electrode mapping system under development by Endocardial Solutions, Inc. Exemplary cryogenic systems may be available from Cryocath, Inc. and from Cryogen, Inc. A suitable cooled RF ablation catheter is sold commercially as the CHILLI®-Cooled Ablation System from Cardiac Pathways Corporation of California. Pulmonary vein isolation systems for use with the invention are now being developed by Atrionix (ultrasound), Irvine Biomedical (ultrasound), and Cardiofocus (laser ablation).

Figure 15:
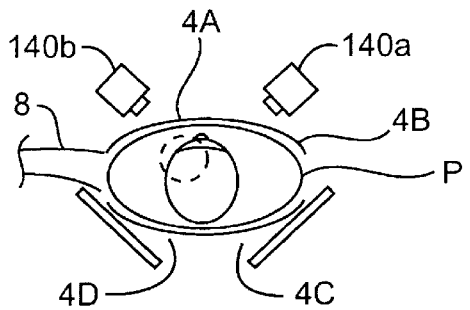
FIG. 15 schematically shows biplane three-dimensional imaging of a patient's heart through imaging windows of a four-panel array system.

Referring now to FIG. 15, biplane fluoroscopic imaging of a heart H within a torso of a patient (using left and right imaging systems 140a, 140b) is illustrated, along with the improved access provided by cables 8 extending off to a common side of the patient. As can be understood with reference to FIG. 15, panel 4A is generally adapted to provide sensor signals from a left front quadrant of patient P, while panels 4B, 4C, and 4D are adapted to provide sensing signals from the right front, right rear, and left rear quadrants of the patient's torso, respectively. As can be understood with reference to FIGS. 15, 9A, and 9D, stimulation electrodes 72 will preferably be positioned along panels 4A and 4D so that a heart H of patient P is disposed therebetween so as to facilitate defibrillation by transmitting an electrical current between the stimulation electrodes.

As was generally described above, it is often beneficial to include adhesives or some alternative mechanism for independently mounting each panel against the torso surface of the patient. While the described peel-and-stick mounting is preferred, alternative independent panel mounting structures (such as separately deposited adhesives, independent straps, and the like) may also be used. Additionally, interpanel attachment mechanisms may also be included such as elastic members extending between panels, releasably attachable straps having buckles, velcro® attachments, and the like may also be provided. In some embodiments, it may be possible to attach the electrodes to a garment and/or garment-like structure. However, it is generally preferably to provide independent mounting, as this enhances the physician's ability to accurately position the sensors of the array supported by each panel. Additionally, it may be difficult to simultaneously align all of the panels upon the patient with a single interconnected structure or garment.

Figure 16:
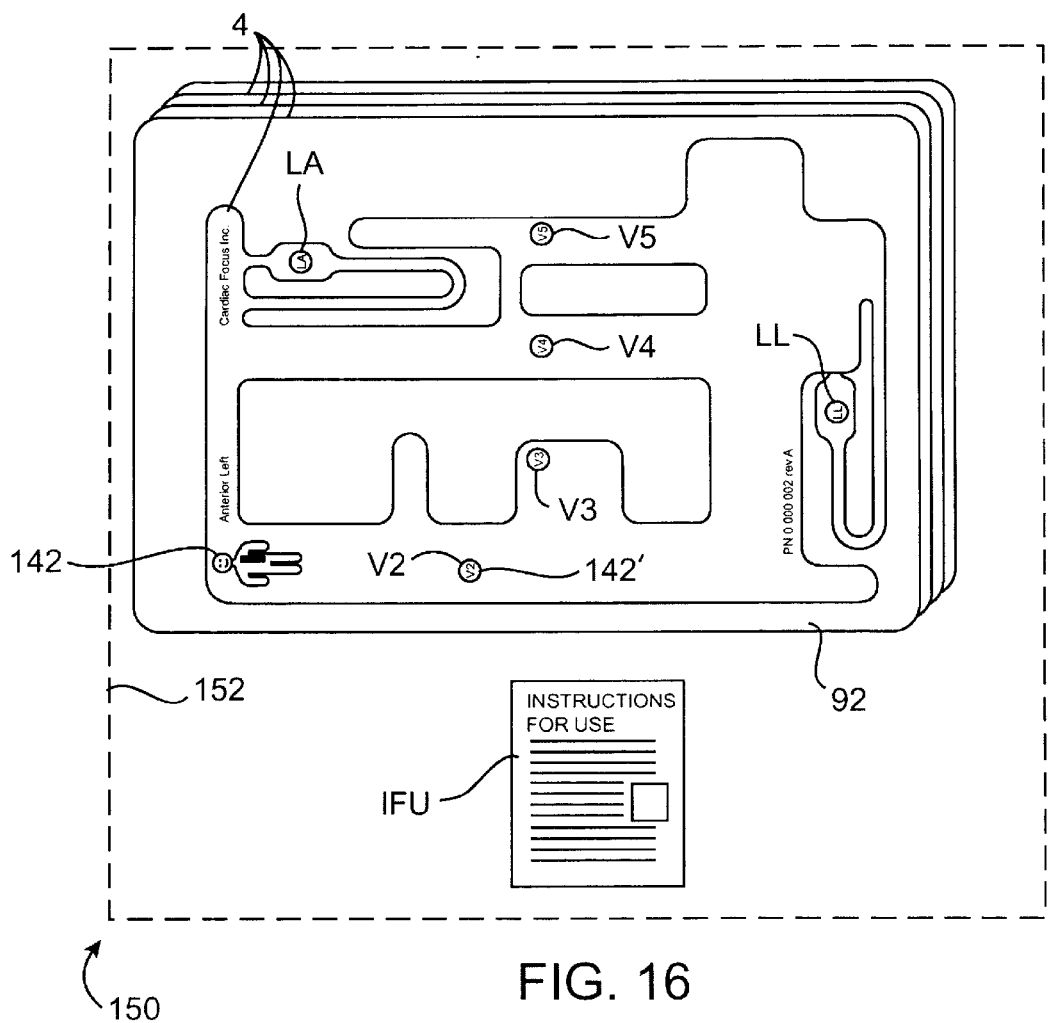
FIG. 16 schematically illustrates a system and/or kit for sensing arrhythmias.

Referring now to FIG. 16, panels 4 will often have writing, graphical pictures, and/or other indicia of panel positioning visible upon one or more of the panels, and/or upon an associated structure, such as upon a peel-away plastic sheet 92. Indicia of alignment 142 will generally indicate a desired position and orientation of at least one panel 4 relative to patient P, and/or relative to an adjacent panel. In the exemplary embodiment, selected electrodes 142' are visibly marked upon the panel outer surface, and may be used to align the panels with the patient's anatomy. More specifically, positioning electrode 142' may be located in the 4th intercostal space, left (for panel 4A) or right (for panel 4B) parasternal. These are the respective standard positions for the V2 and V1 electrode positions in a known standard 12-lead ECG system. The posterior panels (i.e., 4C and 4D) will be positioned so that a bottom edge of these panels is aligned with a bottom edge of an anterior panel (i.e., 4A and/or 4B). As illustrated in FIG. 16, the other standard ECG leads may also be visually indicated on an outer surface of the appropriate panel, including the V3, V4, V5, LA and LL lead locations. In some embodiments, a first panel will be positioned against a patient with reference to physiological reference point, such as the supersternal notch. An adjacent front panel may then be positioned with reference to both the supersternal notch and an alignment marker of the first mounted panel.

Referring once again to FIGS. 15 and 16, a kit 150 for sensing and/or localizing an arrhythmia site of heart H will typically include one or more panels 4 together with instructions for use IFU. Instructions for use IFU and panels 4 will typically be included within packaging 152, the instructions for use optionally being embodied as printed information (in some embodiments appearing at least in part on the packing material, or a sterile wrapping of panels 4), a VCR tape, media embodying a machine-readable code, or the like. Instructions for use IFU will often describe mounting the one or more panels 4 upon patient P, and may also describe localizing an arrhythmia with the mounted panels and/or treatment of the arrhythmia based at least in part on heart signals sensed by the panels.

Referring now to FIGS. 17, 18, 19 and 20, an alternative panel system comprising four panels 160A, 160B, 160C, and 160D (collectively panels 160) include substrates 60 on which sensors 12 are coupled to connector 65 via leads 62, as described above regarding panels 4. However, in these embodiments leads 62 generally directly couple the electrodes of sensors 12 to connector 65 without preprocessing of the signal. Such "passive" panel structures are particularly well suited for a low-noise environment, and/or for ambulatory or long-term tests. These long-term and/or ambulatory data sensing (and as described above, optionally recording) sessions are particularly useful for screening and measurement of arrhythmias and other diseases of the heart before an invasive diagnosis and/or treatment. For example, as described in co-pending provisional patent application serial No. 60/189,611, as filed on Mar. 15, 2000 (the full disclosure of which was previously incorporated by reference), measurements of a heartbeat at or near the initiation of a naturally occurring AFib episode can be particularly beneficial for localization and/or treatment.

As can be understood with reference to the initial recording of the arrhythmia at step 44 and signal comparison of a paced arrhythmia at step 54 in FIG. 2, many treatment protocols and treatment systems will make use of both an active and passive panel system for diagnosis and treatment of a single patient. The panel substrate outlines, sensor structures, and at least some of lead traces 62 from panels 160 may also be used within an active panel system (as described above) so as to avoid the cost and complexity of alternative duplicate parts when fabricating both active and passive panels. Some and/or all of the panel structures may be disposable.

Figure 17A:
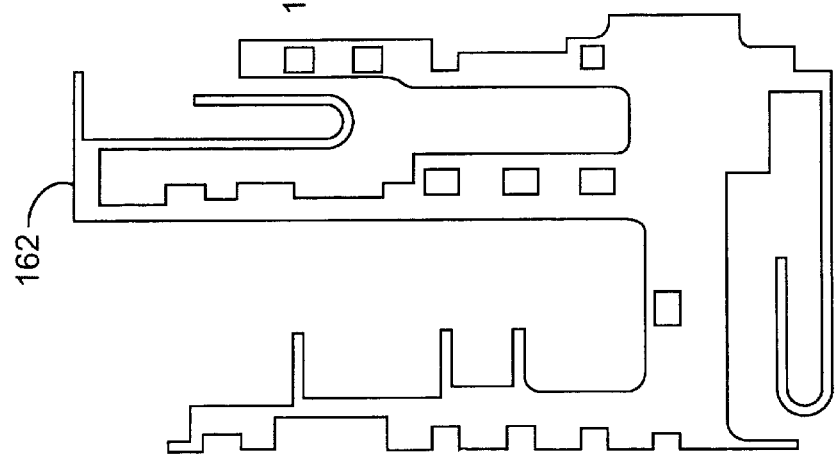
FIGS. 17A–C illustrate additional panel layer structures for use with the passive panel of FIG. 17.
Figure 17B:
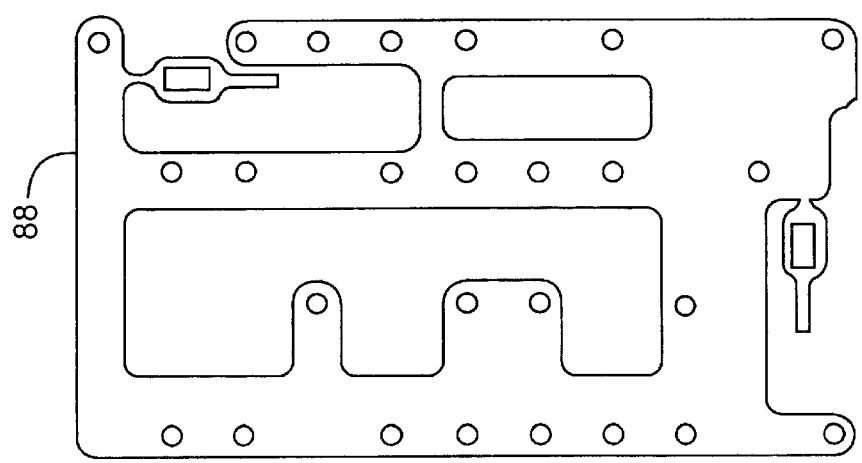
Figure 17C:
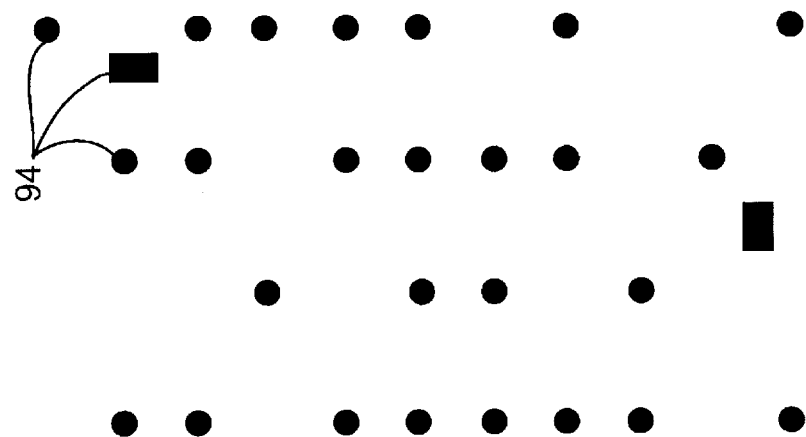
Figure 18:
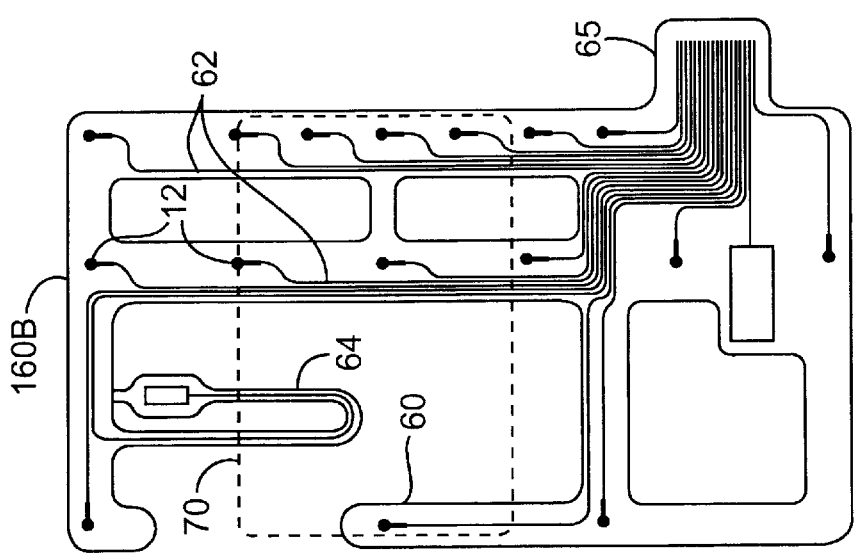
FIGS. 18–20 illustrate exemplary passive panel layouts for use with the panel of FIGS. 17 in a passive four panel set.

A multi-level fabrication method and panel structure can also clearly be understood with reference to FIGS. 17 and 17A–C. Anterior left panel 160A is shown with a substrate base 60 upon which a first deposition layer comprising electrodes 90 and a second deposition layer comprising leads 62 have been deposited in FIG. 17. Over these first two deposited layers, an insulation layer 162 is next deposited (FIG. 17A). Over the insulation an adhesive foam layer 88 is deposited, followed by a layer of conductive gel or adhesive 94 as illustrated in FIG. 17C. Each of these layers is selectively deposited and arranged so as to provide the desired sensor and electrical connection configuration. A peel-away layer 92 (see FIG. 16) helps to protect the adhesive and prevent the gel from drying out. Note that in some embodiments, as illustrated in FIG. 20, connector 65 and/or an associated portion of the panel substrate may extend laterally, particularly along one posterior panel so as to provide a thin, comfortable electrical pathway toward the system analyzer, transmitter, and/or recorder when the patient is laying on his or her back. Suitable structures for coupling cables 8 to connectors 65 include those described, for example, in PCT Application Publication No. WO 97/49143, the full disclosure of which is incorporated by reference, or by a variety of standard widely available flex circuit connectors.

While the exemplary embodiments have been described in some detail, by way of example and for clarity of understanding, a variety of changes, adaptations, and modifications will be obvious to those of skill in the art. Hence, the scope of the present invention is limited solely by the appended claims.

What is claimed is:

1. An arrhythmia or ischemia localization method comprising:
    independently affixing a plurality of panels against a torso of a patient body;
    sensing heart cycle signals with an array of sensors supported by the panels, a plurality of the sensors of the array distributed along a superior-inferior length and distributed along a lateral width of each panel so as to define an at least two dimensional partial-array for each panel;
    generating data in response to the sensed heart signals;
    comparing the data with a database generated from abnormal heartbeats; and
    localizing the arrhythmia or ischemia within a chamber of the heart using the comparison of the data generated from the sensed heart cycle signals with the database.
2. The method of claim 1, wherein the localizing step comprises localizing an arrhythmia within a chamber of the heart with the sensed heart signals.

3. The method of claim 2, further comprising processing the sensed heart cycle signals with a plurality of powered circuits supported by the panels and distributed among the sensors to inhibit signal noise transmission.

4. The method of claim 3, further comprising:
transmitting the sensed heart signals along leads extending between the sensors and the powered circuits; and
transmitting the processed heart cycle signals via electrical conductors along leads extending from the powered circuits to a coupler, wherein the sensor/powered circuit leads are shorter than the powered circuit/connector leads so as to inhibit signal noise.

5. The method of claim 3, further comprising imaging the heart through an imaging window of the panels while sensing the heart cycle signals.

6. The method of claim 5, wherein the imaging step comprises biplanor fluoroscopic imaging of the heart through 4 imaging windows of the panels.

7. The method of claim 5, wherein a plurality of sensors of the array are disposed outside the window, and wherein a sensor of the array is disposed within the window, the sensor within the window having greater transparency for imaging therethrough than the plurality of sensors outside the window.

8. The method of claim 5, further comprising pacing the heart while imaging the heart through the window and while sensing the heart cycle signals with the array.

9. The method of claim 2, further comprising stimulating the heart with an electrode of the panels through the patient's torso.

10. The method of claim 2, further comprising inserting a probe into the patient, engaging a target tissue with the probe, and transmitting therapeutic electrical current from the probe to the target tissue engaged by the probe, and from the patient to a return electrode supported by the panels.

11. The method of claim 2, further comprising separating a cross-member of the panels to alter the panels from a first configuration to a second configuration, the first configuration suitable for an external anatomy different than that of the patient, the second configuration suitable for an external anatomy of the patient.

12. The method of claim 11, wherein the cross-member is disposed between a first sensor of an associated panel and a second sensor of the associated panel, and wherein leads coupled to the sensors of the panel do not traverse the cross-member so as to avoid signal loss when the cross-member is separated.

13. The method of claim 11, wherein the external anatomy different than the patient is a male anatomy, wherein the external anatomy of the patient is a male anatomy, and wherein separation of the cross-member changes the panel from a male configuration to a female configuration so as to maintain electrical coupling between the sensors of the array and the torso while accommodating breasts of the patient.

14. The method of claim 2, wherein the plurality of panels comprises four flexible inelastic panels, the four panels being independently attached to the torso by referring to indicia of alignment displayed upon the panels.

15. The method of claim 14, wherein the plurality of panels comprises no more than 4 panels.

16. The method of claim 15, wherein a sensor of the array is coupled to the patient at a location beyond perimeters of each of the four panels.

17. The method of claim 2, further comprising integrating a reference portion of sensed heart cycle signals at an array of sensing locations during an abnormal heartbeat, generating a first data matrix of the integrated signals, comparing the first data matrix with a database of matrices generated from abnormal heartbeats, pacing a candidate arrhythmia site, generating a paced data matrix of integrated reference portions of paced heart cycle signals, and comparing the paced data matrix with the first data matrix.

18. The method of claim 17, wherein the abnormal heartbeat and paced heart cycle signals are measured with the sensors of a low-noise environment array and the array, respectively, the array being adapted for use in a high electromagnetic noise environment.

19. The method of claim 17, wherein the abnormal heartbeat and paced heart cycle signals are measured with the sensors of the array.

20. The method of claim 2, wherein the localization step further comprises localizing an atrial fibrillation within an atrium of the heart.

21. The method of claim 1,
wherein each panel comprises a flexible substrate supporting the sensors of the partial array, conductive traces disposed on the substrate and coupled to the sensors, adhesive foam distributed along the substrate surrounding and separated from the sensors, and conductive gel adjacent each sensor of the partial array to the torso;
wherein the affixing step comprises independently affixing each panel to the torso by engaging the adhesive foam against the torso so that the conductive gel couples each sensor of the partial array to the adjacent torso; and
further comprising transmitting the sensed heart signals along the conductive traces.

22. The method of claim 1, wherein the database comprises a plurality of candidate sites within the chamber of the heart associated with known abnormal heartbeats, and
wherein the localizing step comprises selecting a site from the plurality of sites.

23. An arrhythmia localization method comprising:
independently affixing a plurality of panels against a torso of a patient body;
sensing heart cycle signals with an array of sensors supported by the panels, a plurality of the sensors of the array distributed along a superior-inferior length and distributed along a lateral width of each panel so as to define an at least two dimensional partial-array for each panel;
generating data in response to the sensed heart signals;
comparing the data with a database generated from abnormal heartbeats; and
localizing atrial fibrillation within an atrium of the heart using the comparison of the data generated from the sensed heart cycle signals with the database.

24. The method of claim 23, further comprising:
transmitting the sensed heart signals along leads extending between the sensors and the powered circuits; and
transmitting the processed heart cycle signals along electrical conductors extending from the powered circuits to a coupler, wherein the sensor/powered circuit leads are shorter than the powered circuit/connector conductors so as to inhibit signal noise.

25. The method of claim 24, further comprising pacing a candidate arrhythmia site while sensing the heart cycle signals.

26. An arrhythmia or ischemia localization method comprising:

adhesively affixing at least one panel against a torso of a patient body by engaging adhesive foam of the panel against the torso;

sensing heart cycle signals with an array of sensors supported by the at least one panel, the at least one panel comprising a flexible substrate supporting a plurality of the sensors of the array, the adhesive foam distributed along the substrate and separated from the sensors with conductive gel coupling the sensors to the torso adjacent the sensors;

transmitting the sensed heart signals along conductive traces disposed on the substrate and localizing the arrhythmia or ischemia within a chamber of the heart using the sensed heart cycle signals.

* * * * *